US009688821B2

(12) United States Patent
Tamura et al.

(10) Patent No.: US 9,688,821 B2
(45) Date of Patent: *Jun. 27, 2017

(54) METHOD OF PRODUCING A LOW ODOR GLYCERIN DERIVATIVE-MODIFIED SILICONE OR A COMPOSITION COMPRISING THE SAME

(71) Applicant: Dow Corning Toray Co., Ltd., Tokyo (JP)

(72) Inventors: Seiki Tamura, Ichihara (JP); Tatsuo Souda, Ichihara (JP); Seiji Hori, Ichihara (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 46 days.

This patent is subject to a terminal disclaimer.

(21) Appl. No.: 14/369,240

(22) PCT Filed: Dec. 26, 2012

(86) PCT No.: PCT/JP2012/084279
§ 371 (c)(1),
(2) Date: Jun. 27, 2014

(87) PCT Pub. No.: WO2013/100176
PCT Pub. Date: Jul. 4, 2013

(65) Prior Publication Data
US 2015/0080480 A1  Mar. 19, 2015

(30) Foreign Application Priority Data
Dec. 27, 2011  (JP) .................................. 2011-286974

(51) Int. Cl.
| *C08G 77/08* | (2006.01) |
| *C08G 77/18* | (2006.01) |
| *A61K 8/892* | (2006.01) |
| *C08G 77/16* | (2006.01) |
| *C08G 77/34* | (2006.01) |
| *C08L 83/06* | (2006.01) |
| *A61Q 1/02* | (2006.01) |
| *A61Q 19/00* | (2006.01) |
| *A61K 8/894* | (2006.01) |
| *A61Q 90/00* | (2009.01) |

(52) U.S. Cl.
CPC .............. *C08G 77/18* (2013.01); *A61K 8/892* (2013.01); *A61K 8/894* (2013.01); *A61Q 1/02* (2013.01); *A61Q 19/00* (2013.01); *A61Q 90/00* (2013.01); *C08G 77/16* (2013.01); *C08G 77/34* (2013.01); *C08L 83/06* (2013.01); *A61K 2800/10* (2013.01)

(58) Field of Classification Search
CPC ........ C08G 77/16; C08G 77/18; C08G 77/34; C08L 83/06
See application file for complete search history.

(56) References Cited

U.S. PATENT DOCUMENTS

| 4,431,789 A | 2/1984 | Okazaki et al. |
| 4,515,979 A | 5/1985 | Otsuki et al. |
| 5,225,509 A | 7/1993 | Heinrich et al. |
| 5,288,831 A | 2/1994 | Ichinohe et al. |
| 2002/0131947 A1 | 9/2002 | Nakanishi |
| 2003/0158363 A1 | 8/2003 | Nakanishi |
| 2004/0253197 A1 | 12/2004 | Sakuta |
| 2005/0008600 A1 | 1/2005 | Nakanishi et al. |
| 2006/0018935 A1 | 1/2006 | Nishijima et al. |
| 2006/0034875 A1* | 2/2006 | Nakanishi .............. A61K 8/891 424/401 |
| 2012/0245305 A1* | 9/2012 | Souda .................... A61K 8/894 525/479 |
| 2012/0269748 A1 | 10/2012 | Tamura et al. |
| 2012/0269875 A1 | 10/2012 | Tamura et al. |

FOREIGN PATENT DOCUMENTS

| EP | 2492300 A1 | 8/2012 |
| JP | 5541210 B2 | 10/1980 |
| JP | S57149290 A | 9/1982 |
| JP | S6018525 A | 1/1985 |
| JP | S62195389 A | 8/1987 |
| JP | H02302438 A | 12/1990 |
| JP | H0689147 B2 | 11/1994 |
| JP | H07330907 A | 12/1995 |

(Continued)

OTHER PUBLICATIONS

International Search Report for PCT/JP2012/084279 dated Oct. 11, 2013, 6 pages.
English language abstract for JPS57149290 extracted from espacenet.com database on Sep. 8, 2014, 2 pages. Also see English equivalent U.S. Pat. No. 4,431,789.
English language abstract for JPS6018525 extracted from espacenet.com database on Sep. 9, 2014, 2 pages. Also see English equivalent U.S. Pat. No. 4,515,979.
English language abstract for JPS62195389 extracted from espacenet.com database on Sep. 8, 2014, 2 pages.
English language abstract for JPH02302438 extracted from espacenet.com database on Sep. 9, 2014, 1 page. Also see English equivalent U.S. Pat. No. 5,288,831.

(Continued)

*Primary Examiner* — Margaret Moore
(74) *Attorney, Agent, or Firm* — Howard & Howard Attorneys PLLC

(57) ABSTRACT

A method of producing a glycerin derivative-modified silicone or a composition comprising the same, including a process that treats the glycerin derivative-modified silicone or the composition comprising the same with one or more type of acidic inorganic salt, which is solid at 25° C. and water soluble, and which is such that a pH at 25° C. of an aqueous solution prepared by dissolving 50 g of the acidic inorganic salt in 1 L of ion exchanged water is 4 or lower; and an external use preparation, cosmetic composition, or raw materials thereof that contain the low odor glycerin derivative-modified silicone obtained by the production method.

16 Claims, No Drawings

(56) References Cited

FOREIGN PATENT DOCUMENTS

| | | |
|---|---|---|
| JP | 2613124 B2 | 5/1997 |
| JP | H09165315 A | 6/1997 |
| JP | H09165318 A | 6/1997 |
| JP | 2844453 B2 | 1/1999 |
| JP | 2002179798 A | 6/2002 |
| JP | 2004339244 A | 12/2004 |
| JP | 2005042097 A | 2/2005 |
| JP | 2005089494 A | 4/2005 |
| JP | 2005120293 A | 5/2005 |
| WO | WO02055588 A1 | 7/2002 |
| WO | WO2004046226 A1 | 6/2004 |
| WO | WO2011049246 A1 | 4/2011 |
| WO | WO2011049247 A1 | 4/2011 |
| WO | WO2011049248 A1 | 4/2011 |
| WO | 2011/068251 * | 6/2011 |
| WO | WO2011068251 A1 | 6/2011 |

OTHER PUBLICATIONS

English language abstract for JPH0689147 extracted from espacenet.com database on Sep. 8, 2014, 2 pages.
English language abstract and machine-assisted English translation for JPH07330907 extracted from espacenet.com database on Sep. 9, 2014, 10 pages.
English language abstract and machine-assisted English translation for JPH09165315 extracted from espacenet.com database on Sep. 9, 2014, 12 pages.
English language abstract and machine-assisted English translation for JPH09165318 extracted from espacenet.com database on Sep. 9, 2014, 12 pages.
English language abstract for JP2613124 extracted from espacenet.com database on Sep. 9, 2014, 2 pages. Machine-assisted English translation extracted from PAJ database on Aug. 27, 2014, 43 pages.
English language abstract and machine-assisted English translation for JP2844453 extracted from espacenet.com database on Sep. 9, 2014, 16 pages.
English language abstract for JP2002179798 extracted from espacenet.com database on Sep. 9, 2014, 2 pages. Also see English equivalent US 2002/0131947.
English language abstract and machine-assisted English translation for JP2004339244 extracted from espacenet.com database on Sep. 9, 2014, 29 pages.
English language abstract for JP2005042097 extracted from espacenet.com database on Sep. 9, 2014, 2 pages. Also see English Equivalent US2005/0008600.
English language abstract and machine-assisted English translation for JP2005089494 extracted from espacenet.com database on Sep. 9, 2014, 18 pages.
English language abstract and machine-assisted English translation for JP2005120293 extracted from espacenet.com database on Sep. 9, 2014, 48 pages.
English language abstract for WO02055588 extracted from espacenet.com database on Sep. 9, 2014, 2 pages. Also see English equivalent US2003/0158363.
English language abstract for WO2004046226 extracted from espacenet.com database on Sep. 9, 2014, 2 pages. Also see English equivalent US 2006/0018935.
English language abstract for WO2011049246 extracted from espacenet.com database on Sep. 8, 2014, 2 pages. Also see English equivalent EP2492300.
English language abstract for WO2011049247 extracted from espacenet.com database on Sep. 9, 2014, 2 pages. Also see English equivalent US 2012/0269748.
English language abstract for WO2011049248 extracted from espacenet.com database on Sep. 8, 2014, 2 pages. Also see English equivalent US 2012/0269875.

\* cited by examiner

METHOD OF PRODUCING A LOW ODOR GLYCERIN DERIVATIVE-MODIFIED SILICONE OR A COMPOSITION COMPRISING THE SAME

CROSS-REFERENCE TO RELATED APPLICATIONS

This application is the National Stage of International Patent Application No. PCT/JP2012/084279, filed on Dec. 26, 2012, which claims priority to and all the advantages of Japanese Patent Application No. 2011-286974, filed on Dec. 27, 2011, the content of which is incorporated herein by reference.

TECHNICAL FIELD

The present invention relates to the reduction of the odor of a glycerin derivative-modified silicone that was modified by a glycerin derivative or a composition comprising the same, and relates to the use of said glycerin derivative-modified silicone or a composition comprising the same as an external use preparation, cosmetic composition and raw materials thereof.

BACKGROUND ART

Silicones having hydrophilic groups exhibit excellent surface activity due to possessing both a silicone moiety, which exhibits properties such as hydrophobicity, softness, lubricity and chemical stability, and a hydrophilic group moiety, which exhibits properties such as hydrophilicity, moisture retention properties and adhesive properties. Therefore, silicones having hydrophilic groups are widely used in foods, resins, coatings, cosmetic compositions and the like, and a variety of hydrophilic silicone compounds have been known in the past. In particular, silicone oils such as low molecular weight cyclic siloxanes are often blended in order to improve the sensation during use of a cosmetic composition, and polyether-modified silicones (polyether-modified polysiloxanes) are widely used as cosmetic composition raw materials such as surfactants due to exhibiting good compatibility with silicone oils.

On the other hand, aside from polyether-modified (polyoxyalkylene-modified) silicone, glycerin-modified silicone also is known as a nonionic hydrophilic silicone (Patent Documents 1 through 9). However, there are considerable technical difficulties associated with the stable production of glycerin-modified silicone as a raw material for cosmetic compositions or external use preparations. Unsaturated group-containing glycerin derivative, a raw material of glycerin-modified silicone, is comparatively expensive and difficult to obtain on a commercial scale, and its application is limited. Furthermore, as will be discussed below, there are unsolved problems associated with the reduction of the odor of a glycerin-modified silicone.

In recent years, glycerin-modified groups have attracted attention because their oxidative stability and feeling to touch are both superior to those of polyether-modified (polyoxyalkylene-modified) groups. The applicant of the present application also proposes the use of silicones having glycerin and other hydrophilic modified groups as cosmetic composition raw materials (Patent Documents 20 and 21).

Such glycerin-modified silicone or compositions comprising the same can be synthesized by, for example, a hydrosilylation reaction between an organohydrogenpolysiloxane having a silicon-bonded hydrogen group and a glycerin derivative group-containing compound having a carbon-carbon double bond. However, glycerin-modified silicone or compositions comprising the same sometimes have an aldehyde like odor. The odor increases readily particularly because of the effects of the passage of time, the temperature, and water, so problems sometimes occur in its use in applications of external use preparations and cosmetic compositions applied to the human body. In addition, even when it is possible to incorporate glycerin-modified silicone or compositions comprising the same in an external use preparation or a cosmetic composition, there are problems such as its incorporation amount being restricted. As a result, the applicant of the present application has also proposed and specifically disclosed in the above documents that a publicly known odor reduction method and purification method such as acidizing and hydrogenation are preferable when using a silicone having glycerin or another hydrophilic modified group of the application as an external use preparation or a cosmetic composition (Patent Documents 20 and 21). These treatments were able to reduce odors and yielded silicones having a hydrophilic modified group, which was suitable for use as a cosmetic composition raw material.

On the other hand, a great deal of research into reducing the odor of polyether-modified polysiloxanes (polyoxyalkylene group-containing organopolysiloxanes) has been conducted so far. The cause of odorization over time of a polyether-modified polysiloxane that was first reported was the aldehyde and acid produced as a result of oxidation degradation (rancidity) over time of the polyether moiety in the polyether-modified polysiloxane composition. Examples of technologies to suppress this oxidation degradation include the methods recited in Patent Documents 10 and 11 in which tocopherol, phytic acid, or a similar antioxidant component is added to the polyether-modified polysiloxane composition.

However, the use of only an anti-oxidizing agent results in the insufficient suppression of the odorization over time of a formulation based on the polyether-modified polysiloxane and, as a result, other causes were investigated. As a result, Patent Document 12 recites that propionaldehyde originating from unreacted propenyl-etherified polyoxyalkylene is a cause of the odor.

The polyether-modified polysiloxane composition is typically synthesized via a hydrosilylation reaction of an organohydrogenpolysiloxane having a silicon-bonded hydrogen group and a polyoxyalkylene having an allyl ether group at a terminal. Patent Document 12 recites that, in the production of the polyether-modified polysiloxane composition, a double bond of the allyl etherified polyoxyalkylene migrates inward due to the influence of a platinum catalyst and a portion of the allyl-etherified polyoxyalkylene becomes a propenyl-etherified polyoxyalkylene and remains in the polyether-modified polysiloxane composition as is without reacting with the organohydrogenpolysiloxane. Patent Document 12 also recites that the propenyl-etherified polyoxyalkylene degrades over time, thus producing ketones and aldehydes which results in the odorization. Moreover, hydrolysis in the presence of an acid is disclosed as a useful deodorization method.

However, while this deodorization method could be thought to be useful if all of the allyl groups of the polyoxyalkylene remaining in the composition were replaced with propenyl groups, in actuality, a significant proportion of the allyl-etherified polyoxyalkylene which is not easily hydrolyzed remains. As a result, the composition cannot be sufficiently deodorized using the deodorization method of Patent Document 12. On the other hand, if a strong acid is used that can hydrolyze the allyl-etherified polyoxyalkylene, the carbon-oxygen bond at the polyoxyalkylene site and/or the silicon-oxygen bond at the polysiloxane site may disconnect, so using such an acid is inappropriate. Additionally, in order to perform the hydrolysis reaction in a quantitative manner, excessive amounts of water and acid are needed. These excessive amounts of water and acid complicate post treatment processes and, therefore, this deodorization method is not preferable.

In order to resolve this problem, methods for suppressing the production of propionaldehyde have been disclosed (Patent Documents 13 to 16). In these methods, a hydrogenation treatment is performed as a deodorization method of the polyether-modified polysiloxane composition in order to alkylate the alkenyl groups (double bonds) included in the alkenyl group-containing polyoxyalkylene (including both propenyl-etherified polyoxyalkylene and allyl-etherified polyoxyalkylene) remaining in the composition. However, even with a polyether-modified polysiloxane composition deodorized using a hydrogenation reaction, in cases where a formulation including water and an alcohol is compounded, it may be difficult to achieve sufficient deodorization over time or under elevated temperature conditions.

A cause of the odorization is acetal and similar aldehyde condensation products that are free of unsaturated bonds that remain in the composition. Thus, for the purpose of completely eliminating the acetal and other aldehyde condensation products, technology in which treatment using the acid aqueous solution and hydrogenation treatment are combined (Patent Document 17); and technologies in which hydrogenation treatment and treatment using a solid acid catalyst are combined (Patent Documents 18 and 19) are disclosed. The technology recited in Patent Document 17 is applied not only to polyether-modified silicones, but also to glycerin-modified silicones and sugar-modified silicones. That is, it is acknowledged that performing at least hydrogenation treatment is preferable in the deodorization of hydrophilic silicones as a raw material suitable for use in cosmetic products.

However, hydrogenation treatment requires dedicated special equipment and catalysts. Furthermore, silicones modified with polyhydric alcohols such as sugar and glycerin derivatives have much higher viscosities than viscosities of general polyether-modified silicones, so it is essential to dilute with a large quantity of solvent, from the perspectives of production time reduction and reaction efficiency when performing hydrogenation treatment. These are the principal reasons that the cost of polyhydric alcohol-modified silicone, which was high to begin with, has increased further, and that commercial sales of said modified silicone are stagnating.

Thus, in odor reduction treatments such as acid aqueous solution based treatments that can be performed comparatively inexpensively, it is difficult to reduce the odor of glycerin-modified silicone or a composition comprising the same, as a raw material suitable for cosmetic compositions. When hydrogenation treatment for further odor reduction is required, it generally becomes a drawback with respect to processing and cost.

Furthermore, given the cost drawback, even when hydrogenation treatment is performed by applying hydrogenation equipment such as that used for polyether-modified silicone, glycerin-modified silicone generally is highly viscous, and a solvent removal process and dilution treatment unnecessary for polyether-modified silicone, such as dilution with a large quantity of solvent, become necessary. Not only does this result in an additional cost related drawback, but there are problems related to safety and the increase in the environmental burden associated with the use of large quantities of solvent. In addition to the technical drawbacks, these are factors that further increase the costs of industrial products, with respect to environment and business management.

As a result, for the glycerin-modified silicone or compositions comprising the same, it remains technically very difficult to reduce the odor of the raw materials of cosmetic compositions and external use preparations. Furthermore, the cost increase associated with odor reduction becomes a burden, and compared with normal polyether-modified silicone, it is difficult to supply refined products with sharply reduced odor, at a low price and in large quantity. Regardless of its superior performance, it has not been widely adopted in the market, which is a problem. As a result, to have glycerin-modified silicone widely adopted in the market, there is a demand for technical development that inexpensively and simply enables a high level of deodorization of glycerin-modified silicone, without performing odor reduction treatment that uses expensive and special equipment such as hydrogenation treatment. In this regard, there is still some room for improvement in the hydrophilic silicone odor reduction treatments proposed by the applicant of the present application in the past (Patent Documents 20, 21).

PRIOR ART DOCUMENTS

Patent Documents

Patent Document 1: Japanese Examined Patent Application Publication No. S-62-34039
Patent Document 2: Japanese Unexamined Patent Application Publication No. S-62-195389
Patent Document 3: Japanese Examined Patent Application Publication No. H-06-089147
Patent Document 4: Japanese Patent No. 2613124 (Japanese Unexamined Patent Application Publication No. H-04-188795)
Patent Document 5: Japanese Patent No. 2844453 (Japanese Unexamined Patent Application Publication No. H-02-228958)
Patent Document 6: Japanese Patent No. 3976226 (Japanese Unexamined Patent Application Publication No. 2002-179798)
Patent Document 7: Japanese Unexamined Patent Application Publication No. 2004-339244
Patent Document 8: Japanese Unexamined Patent Application Publication No. 2005-042097
Patent Document 9: Japanese Unexamined Patent Application Publication No. 2005-089494
Patent Document 10: Japanese Examined Patent Application Publication No. S-55-041210
Patent Document 11: Japanese Unexamined Patent Application Publication No. S-60-018525
Patent Document 12: Japanese Unexamined Patent Application Publication No. H-02-302438
Patent Document 13: U.S. Pat. No. 5,225,509
Patent Document 14: Japanese Unexamined Patent Application Publication No. H-07-330907
Patent Document 15: Japanese Unexamined Patent Application Publication No. H-09-165315
Patent Document 16: Japanese Unexamined Patent Application Publication No. H-09-165318
Patent Document 17: WO2002/055588
Patent Document 18: WO2004/046226
Patent Document 19: Japanese Unexamined Patent Application Publication No. 2005-120293
Patent Document 20: WO2011/049247
Patent Document 21: WO2011/049248

DISCLOSURE OF INVENTION

Technical Problems

The present invention was developed to solve the aforementioned problems. The first object of the present invention is to provide a method of producing a low odor glycerin derivative-modified silicone that is inexpensive, allows large batch odor reduction treatment to be performed simply and all at once, has minimal odor, and that also has suppressed odorization in the formulation and over time.

Moreover, the second object of the present invention is to provide external use preparations and cosmetic compositions that apply such low odor glycerin derivative-modified silicone, as well as raw materials thereof.

Furthermore, one reason for the odor of a glycerin derivative-modified silicone is believed to be that, during the hydrosilylation reaction, internal displacement of carbon-carbon double bonds occurs, generating propionaldehyde and other carbonyl compounds. The third object of the present invention is to provide a method of accurately and simply quantitating such carbonyl compounds, and to provide a low odor glycerin derivative-modified silicone or a composition comprising the same, having a carbonyl value of less than or equal to 3.0 Abs/g, as measured by said method.

Solution to Problems

As a result of diligent research, the inventors of the present invention completed the present invention. That is, the first object of the present invention is achieved by a method of producing a glycerin derivative-modified silicone or a composition comprising the same, including a process that treats the glycerin derivative-modified silicone or the composition comprising the same with one or more type of acidic inorganic salt, which is solid at 25° C. and water soluble, and which is such that a pH at 25° C. of an aqueous solution prepared by dissolving 50 g of the acidic inorganic salt in 1 L of ion exchanged water is 4 or lower. It is preferable to include a process that removes odor-causing substances by heating and depressurizing after said treatment process that uses an acidic inorganic salt.

In addition, the first object of the present invention can be preferably achieved by using at least one acidic inorganic salt selected from among the group comprising sodium hydrogensulfate, potassium hydrogensulfate, and ammonium hydrogensulfate, in said production method. The treatment process that uses the acidic inorganic salt is more preferably carried out in the presence of water or a hydrophilic solvent.

In particular, the first object of the present invention can be satisfactorily achieved by a method of producing a glycerin derivative-modified silicone or a composition comprising the same, characterized by the further addition of an alkaline buffer, in an amount corresponding to 100 ppm to 50,000 ppm, to the glycerin derivative-modified silicone or the composition comprising the same that was obtained by a production method that includes the treatment process based on the aforementioned organic salt.

The second object of the present invention is achieved by a cosmetic composition or external use preparation that contains the glycerin derivative-modified silicone obtained by the above production method or a composition comprising the same, or by the raw materials thereof.

The third object of the present invention is achieved by a method that measures the carbonyl value of a glycerin derivative-modified silicone or composition comprising the same, based on the absorbance of a reaction solution obtained by reacting 2,4-dinitrophenylhydrazine and the carbonyls in the glycerin derivative-modified silicone or the composition comprising the same, which was obtained by the above production method, in a reaction medium containing at least one monovalent lower alcohol having 1 to 4 carbon atoms, and by a low odor glycerin derivative-modified silicone or a composition comprising the same, whose carbonyl value measured by said method is less than or equal to 3.0 Abs/g.

That is, the above-mentioned objectives can be achieved by:

"[1] A method of producing a glycerin derivative-modified silicone or a composition comprising the same, the method comprising a process for treating a glycerin derivative-modified silicone or a composition comprising the same with at least one type of acidic inorganic salt, characterized by the acidic inorganic salt being solid at 25° C. and water soluble, and a pH at 25° C. of an aqueous solution prepared by dissolving 50 g of the acidic inorganic salt in 1 L of ion exchanged water being 4 or lower.

[2] A method of producing a glycerin derivative-modified silicone or a composition comprising the same, wherein the method of producing a glycerin derivative-modified silicone or a composition comprising the same described in [1] above further comprises a process [A] that synthesizes a glycerin derivative-modified silicone or a composition comprising the same by subjecting to a hydrosilylation reaction:
(a) a glycerin derivative having a carbon-carbon double bond at a terminal of the molecular chain and
(b) an organohydrogenpolysiloxane; and
a process [B] that, together with synthesis process [A] or after synthesis process [A], treats glycerin derivative-modified silicone or a composition comprising the same in the presence of at least one type of (c) acidic inorganic salt, characterized by the acidic inorganic salt being solid at 25° C. and water soluble, and a pH at 25° C. of an aqueous solution prepared by dissolving 50 g of the acidic inorganic salt in 1 L of ion exchanged water being 4 or lower.

[3] The method of producing a glycerin derivative-modified silicone or a composition comprising the same described in [1] or [2], comprising a process that removes odor-causing substances by heating or depressurizing after a treatment process that uses the acidic inorganic salt.

[4] The method of producing a glycerin derivative-modified silicone or a composition comprising the same described in any of [1] through [3], wherein the acidic inorganic salt is at least one type of acidic inorganic salt comprising hydrogensulfate ions (NSW) and monovalent cations (W).

[5] The method of producing a glycerin derivative-modified silicone or a composition comprising the same described in any of [1] through [4], wherein the acidic inorganic salt is at least one type of acidic inorganic salt selected from the group comprising sodium hydrogensulfate, potassium hydrogensulfate, and ammonium hydrogensulfate.

[6] The method of producing a glycerin derivative-modified silicone or a composition comprising the same described in any of [1] through [5], characterized by the used amount of the acidic inorganic salt being in a range from 100 ppm to 10,000 ppm for the glycerin derivative-modified silicone or a composition comprising the same.

[7] The method of producing a glycerin derivative-modified silicone or a composition comprising the same described in any of [1] through [6], characterized by performing the treatment process that uses the acidic inorganic salt in the presence of water and/or a hydrophilic medium.

[8] A method of producing a glycerin derivative-modified silicone or a composition comprising the same, characterized by further adding an alkaline buffer, in an amount corresponding to 100 ppm to 50,000 ppm, to the glycerin derivative-modified silicone or a composition comprising the same obtained by the method described in any of [1] through [7].

[9] The method of producing a glycerin derivative-modified silicone or a composition comprising the same described in any one of [1] through [8], wherein the glycerin derivative-modified silicone is a glycerin derivative-modified silicone expressed by the following general formula (1):

(1)

(wherein $R^1$ represents a monovalent organic group (however, excluding $R^2$, L, and Q), a hydrogen atom or a hydroxyl group; and $R^2$ is a substituted or unsubstituted, straight or branched monovalent hydrocarbon group having 9 to 60 carbon atoms, or the chain organosiloxane group represented by the following general formula (2-1):

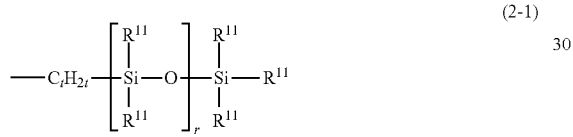
(2-1)

(wherein $R^{11}$ are each independently a substituted or unsubstituted monovalent hydrocarbon group having from 1 to 30 carbons, hydroxyl groups, or hydrogen atoms and at least one of the $R^{11}$ moieties is the monovalent hydrocarbon group; t is a number in a range of 2 to 10; and r is a number in a range of 1 to 500); or the general formula (2-2) below:

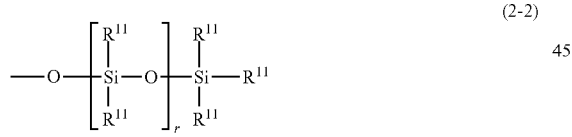
(2-2)

(wherein, $R^{11}$ and r are synonymous with those described above); and $L^1$ represents a silylalkyl group having a siloxane dendron structure expressed by the following general formula (3) when i=1;

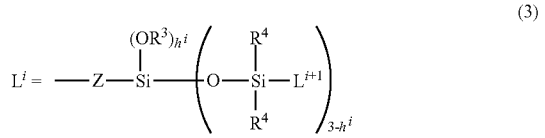
(3)

(wherein, $R^3$ each independently represents a substituted or unsubstituted, straight or branched monovalent hydrocarbon group having 1 to 30 carbons; $R^4$ each independently represents an alkyl group or phenyl group having 1 to 6 carbon atoms; Z represents a divalent organic group; i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^4$ when i=k, and $h^i$ is a number in a range from 0 to 3); Q represents a glycerin derivative group-containing organic group; and a, b, c, and d are numbers within the respective ranges $1.0 \leq a \leq 2.5$, $0 \leq c \leq 1.5$, and $0.0001 \leq d \leq 1.5$).

[10] The method of producing a glycerin derivative-modified silicone or a composition comprising the same that is described in [9], wherein, in general formula (1), the silylalkyl group having the siloxane dendron structure indicated by $L^1$ is a functional group expressed by general formula (3-1) below:

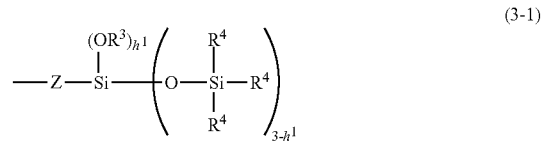
(3-1)

or general formula (3-2) below:

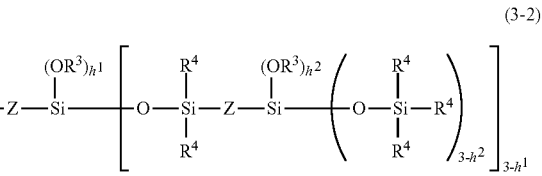
(3-2)

(wherein, $R^3$, $R^4$, and Z are synonymous with those described above, and $h^1$ and $h^2$ are each independently a number in a range from 0 to 3).

[11] The method of producing a glycerin derivative-modified silicone or a composition comprising the same described in [9] or [10], wherein, in general formula (1), Q is a glycerin derivative group-containing organic group that is bonded to a silicon atom via a linking group that is at least divalent, and that contains at least one type of hydrophilic unit that is selected from among the hydrophilic units represented by the following structural formulae (3-3) through (3-5).

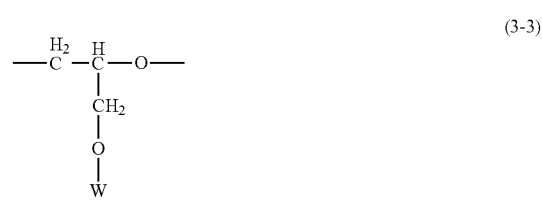
(3-3)

(wherein, W is a hydrogen atom or an alkyl group having from 1 to 20 carbon atoms)

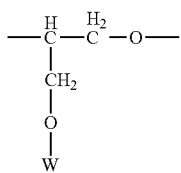

(3-4)

(wherein, W is synonymous with the group described above)

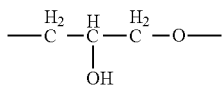

(3-5)

[12] The method of producing a glycerin derivative-modified silicone or a composition comprising the same that is described in any one of [9] through [11], wherein, in general formula (1), Q is a hydrophilic segment that is bonded to a silicon atom via a linking group that is at least divalent, and the hydrophilic segment comprising at least one linearly bonded hydrophilic unit is selected from among the hydrophilic units represented by structural formulae (3-3) through (3-5); or Q is a glycerin derivative group-containing organic group that is bonded to a silicon atom via a linking group that is at least divalent, that contains at least two of one or more type of hydrophilic unit selected from the hydrophilic units represented by structural formulae (3-3) through (3-5), and a branch unit selected from groups represented by structural formulae (3-6) through (3-8).

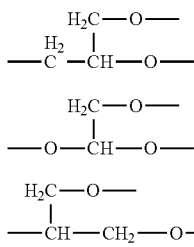

(3-6)

(3-7)

(3-8)

[13] An external use preparation raw material or cosmetic composition raw material comprising the glycerin derivative-modified silicone or a composition comprising the same obtained by the production method described in any of [1] through [12].

[14] An external use preparation or cosmetic composition comprising the glycerin derivative-modified silicone or a composition comprising the same obtained by the production method described in any of [1] through [12].

[15] The external use preparation, cosmetic composition or raw materials thereof described in [13] or [14], comprising an alkaline buffer in an amount corresponding to 100 ppm to 50,000 ppm, for the glycerin derivative-modified silicone or a composition comprising the same.

[16] A method of measuring a carbonyl value of the glycerin derivative-modified silicone or a composition comprising the same, based on the absorbance of a reaction solution that is obtained by reacting, in a reaction medium containing at least one type of monovalent lower alcohol having 1 to 4 carbon atoms, 2,4-dinitrophenylhydrazine and the carbonyls in the glycerin derivative-modified silicone or a composition comprising the same obtained by the production method described in any of [1] through [12].

[17] A glycerin derivative-modified silicone or a composition comprising the same, which is the glycerin derivative-modified silicone or a composition comprising the same obtained by the production method described in any of [1] through [12], wherein the carbonyl value measured by the carbonyl value measurement method described in [16] is less than or equal to 3.0 Abs/g."

Advantageous Effects of Invention

The production method of the present invention is a method that enables odor reduction treatment that is inexpensive and allows large batch odor reduction treatment to be performed simply and all at once. Because the carbon-oxygen bond and silicon-oxygen bond rarely break, the production method has almost no adverse affects on the chemical structure of the obtained low odor glycerin derivative-modified silicone. Furthermore, the low odor glycerin derivative-modified silicone or a composition comprising the same obtained by the production method of the present invention has little odor, and odorization is also suppressed in the formulation and over time, so it is suitable for use in external use preparations and in cosmetic composition applications such as hair cosmetic composition products and skin cosmetic composition products.

The odor reduction effect of the glycerin derivative-modified silicone or compositions comprising the same of the present invention is extremely high, and it can provide an odor reduction effect rivaling that of hydrogenation treatment. On the other hand, hydrogenation treatment is a complex process, and requires comparatively expensive catalysts and special apparatus. On the whole, a glycerin derivative-modified silicone with high viscosity particularly requires considerable amount of solvent, which is a major cost related drawback. The present invention is advantageous in industrial scale implementation because implementation of such hydrogenation treatment is not necessary. Moreover, the present invention can provide a glycerin derivative-modified silicone or a composition comprising the same having sharply reduced odors simply and at low cost.

In addition, through the present invention, it is possible to provide the raw materials for an external use preparation or a cosmetic composition that contains a glycerin derivative-modified silicone or a composition comprising the same and that has an imperceptible characteristic odor. Furthermore, through the present invention, it is possible to provide a cosmetic composition or an external use preparation that comprises said composition and that has very little odor.

The low odor glycerin derivative-modified silicone or a composition comprising the same of the present invention has reduced odor. Therefore masking of an odor is unnecessary when incorporating into an external use preparation or a cosmetic composition, and there is considerable flexibility in the design of the formulations of an external use preparation or a cosmetic composition. This is particularly advantageous in cosmetic compositions, in which functions that contain an odor are emphasized, and, therefore, design of a fragrance free cosmetic composition, a faintly scented cosmetic composition, or a cosmetic composition with a desired fragrance is easy.

In the present invention, it is possible to accurately and simply quantitate carbonyl compounds, which are believed to be a reason for the odor of a glycerin derivative-modified silicone. Additionally, because it is not necessary to perform a sensory test, it is possible to safely and objectively quantify the degree of odor reduction, and it is possible to explicitly state that the odor of a particular product is reduced in various products that are external use preparations, cosmetic compositions, or raw materials thereof.

DESCRIPTION OF EMBODIMENTS

Next, the method of producing the low odor glycerin derivative-modified silicone of the present invention will be described in detail.

(Method of Producing a Low Odor Glycerin Derivative-modified Silicone)

The present invention relates to a method of producing a glycerin derivative-modified silicone or a composition comprising the same, including a process that treats the glycerin derivative-modified silicone or the composition comprising the same with one or more type of acidic inorganic salt, which is solid at 25° C. and water soluble, and which is such that a pH at 25° C. of an aqueous solution prepared by dissolving 50 g of the acidic inorganic salt in 1 L of ion exchanged water is 4 or lower.

From the perspectives of more effectively reducing odor and industrially obtaining the raw materials for an odor reduced external use preparation or cosmetic composition (a glycerin derivative-modified silicone or a composition comprising the same), a particularly preferable production method of the present invention is the method that produces a glycerin derivative-modified silicone or a composition comprising the same, comprising a process [A] that synthesizes a glycerin derivative-modified silicone or a composition comprising the same by subjecting to a hydrosilylation reaction (a) a glycerin derivative having a carbon-carbon double bond at a terminal of the molecular terminals, and (b) an organohydrogenpolysiloxane; and, together with synthesis process [A] or after synthesis process [A], a process [B] that processes the glycerin derivative-modified silicone or the composition comprising the same in the presence of at least one type of acidic inorganic salt, which is solid at 25° C. and water soluble, and which is such that a pH at 25° C. of an aqueous solution prepared by dissolving 50 g of the acidic inorganic salt in 1 L of ion exchanged water is 4 or lower. Additionally, in the method of producing a glycerin derivative-modified silicone, it is more preferable to have a process that removes odor-causing substances, by heating and/or depressurizing after the acidizing process.

(Glycerin Derivative-Modified Silicone)

The glycerin derivative-modified silicone can be expressed by the following general formula (1):

(In the formula,
R$^1$ represents a monovalent organic group (however, excluding R$^2$, L$^1$, and Q), a hydrogen atom, or a hydroxyl group; and
R$^2$ is a substituted or unsubstituted, straight or branched monovalent hydrocarbon group having 9 to 60 carbon atoms, or the chain organosiloxane group represented by the following general formula (2-1):

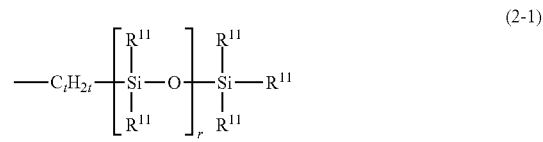

(In the formula, R$^{11}$ are each independently substituted or unsubstituted monovalent hydrocarbon groups having from 1 to 30 carbons, hydroxyl groups, or hydrogen atoms and at least one of the R$^{11}$ moieties is the monovalent hydrocarbon group; t is a number in a range of 2 to 10; and r is a number in a range of 1 to 500); or the general formula (2-2) below:

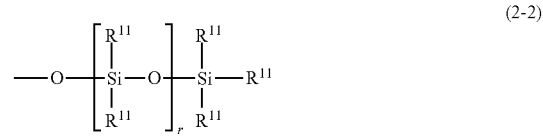

(In the formula, R$^{11}$ and r are synonymous with those described above); and
L$^1$ represents a silylalkyl group having the siloxane dendron structure expressed by the following general formula (3) when i=1;

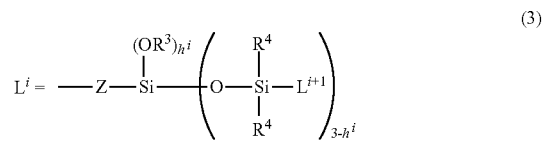

(In the formula,
R$^3$ each independently represents a substituted or unsubstituted, straight or branched monovalent hydrocarbon group having 1 to 30 carbon atoms;
R$^4$ each independently represents an alkyl group or phenyl group having 1 to 6 carbon atoms;
Z represents a divalent organic group;
i represents a generation of the aforementioned silylalkyl group represented by L$^1$ and is an integer of 1 to k when k is a number of generations that is a number of repetitions of the silylalkyl group; the number of generations k is an integer from 1 to 10; L$^{i+1}$ is the silylalkyl group when i is less than k, and R$^4$ when i=k, and h$^i$ is a number in a range from 0 to 3);
Q represents a glycerin derivative group-containing organic group; and
a, b, c, and d are numbers within the respective ranges 1.0≤a≤2.5, 0≤b≤1.5, 0≤c≤1.5, and 0.0001≤d≤1.5).

Here, if the glycerin derivative-modified silicone expressed by general formula (1) has the long chain organic group or the chain organosiloxane group represented by R$^2$, b is a number greater than 0, preferably 0.0001≤b≤1.5, and more preferably 0.001≤b≤1.5. Similarly, if glycerin derivative-modified silicone has a silylalkyl group having the siloxane dendron structure represented by L$^1$, c is a number greater than 0, preferably 0.0001≤c≤1.5, and more preferably 0.001≤c≤1.5.

It is possible to more satisfactorily reduce odors by using the method of producing a glycerin derivative-modified silicone or a composition comprising the same of the present invention for a glycerin derivative-modified silicone that has a long chain organic group or a chain organosiloxane group represented by $R^2$, or a silylalkyl group having a siloxane dendron structure represented by $L^1$, together with a glycerin derivative group-containing organic group (i.e., Q), therefore this is preferable.

At this time, the suitable values of b and c are expressed as follows by essential functional groups.
(1) When there is a group represented by $R^2$: $0.001 \leq b \leq 1.5$ and $0 \leq c \leq 1.5$.
(2) When there is a group represented by $L^1$: 023 $b \leq 1.5$ and $0.001 \leq c \leq 1.5$.
(3) When there are both a group represented by $R^2$ and a group represented by $L^1$: $0.001 \leq b \leq 1.5$ and $0.001 \leq c \leq 1.5$.

The monovalent organic groups, which are $R^1$ of general formula (1), can be the same or different, and they are not particularly limited provided that they are not a functional group of $R^2$, $L^1$, and Q. However, they preferably are a substituted or unsubstituted, straight or branched monovalent hydrocarbon group having 1 to 8 carbon atoms, a polyoxyalkylene group expressed by $-R^5O\,(AO)_n R^6$ (in the formula, AO represents an oxyalkylene group with 2 to 4 carbon atoms; $R^5$ represents a substituted or unsubstituted, straight or branched divalent hydrocarbon group with 3 to 5 carbon atoms; $R^6$ represents a substituted or unsubstituted, straight or branched monovalent hydrocarbon group with 1 to 24 carbon atoms and hydrogen atoms, or a substituted or unsubstituted, straight or branched acyl group with 2 to 24 carbon atoms; and n is 1 to 100), an alkoxy group, a (meth)acryl group, an amide group, a carbinol group, or a phenolic group. However, not all $R^1$ become a hydroxyl group, a hydrogen atom, the alkoxy group, or the polyoxyalkylene group.

Examples of a monovalent hydrocarbon group with 1 to 8 carbon atoms are, for example, alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group having an epoxy group, a glycidyl group, an acyl group, a carboxyl group, an amino group, a (meth)acryl group, a mercapto group, or the like (however, the total number of carbons is from 1 to 8). The monovalent hydrocarbon group is preferably a group other than an alkenyl group, and is more preferably a methyl group, an ethyl group, or a phenyl group. Additionally, examples of the alkoxy group include a methoxy group, an ethoxy group, an isopropoxy group, a butoxy group, and similar lower alkoxy groups; a lauryl alkoxy group, a myristyl alkoxy group, a palmityl alkoxy group, an oleyl alkoxy group, a stearyl alkoxy group, a behenyl alkoxy group, and similar higher alkoxy groups; and the like.

Particularly, the $R^1$ moieties are preferably monovalent hydrocarbon groups having from 1 to 8 carbons and that are free of unsaturated aliphatic bonds or monovalent fluorinated hydrocarbon groups. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is preferably a methyl group, an ethyl group, or a phenyl group, and more preferably from 90 mol % to 100 mol % of all the $R^1$ moieties are selected from methyl groups, ethyl groups, or phenyl groups.

A glycerin derivative-modified silicone aims at imparting additional functionality, and it is possible to introduce or design a modified group other than a hydrophilic group (-Q), particularly a short chain or medium chain hydrocarbon based group, as $R^1$. Specifically, when $R^1$ is a substituted monovalent hydrocarbon group, a substituent can be preferably selected in accordance with desired characteristics and uses. For example, when using the glycerin derivative-modified silicone as a cosmetic composition raw material, it is possible to introduce an amino group, amide group, aminoethyl aminopropyl group, carboxyl group, and the like, as the substituted group of a monovalent hydrocarbon group, for the purpose of improving the sensation during use, feeling to touch, persistence, and the like.

The substituted or unsubstituted, straight or branched monovalent hydrocarbon group having 9 to 60 carbon atoms of $R^2$ of general formula (1) is a long chain hydrocarbon group or a chain organosiloxane group represented by general formula (2-1) or (2-2). By introducing this group at the main chain and/or side chain of polysiloxane, it is possible to further improve the affinity, emulsifiability, and dispersibility, and further the sensation during use of various components such as an oil agent, powder, or the like incorporated in an external use preparation or a cosmetic composition. Furthermore, because the monovalent long chain hydrocarbon group or chain organopolysiloxane group is a hydrophobic functional group, the compounding stability and the compatibility with organic oils having a high content of alkyl groups are further improved. $R^2$ may be all the monovalent long chain hydrocarbon group or all the chain organopolysiloxane group, or may be a functional group of both of these groups. In the glycerin derivative-modified silicone, it is particularly preferable that part or all of $R^2$ is a monovalent long chain hydrocarbon group, and by having such a monovalent long chain hydrocarbon group in a molecule, the glycerin derivative-modified silicone exhibits more superior compatibility not only with silicone oil, but with non silicone oil with a high alkyl group content as well. For example, it is possible to obtain an emulsion and a dispersion with superior stability over time and thermal stability, which are made of non silicone oil.

Substituted or unsubstituted, straight or branched monovalent hydrocarbon groups that are represented by $R^2$ of general formula (1), that are bonded to silicon atoms, and that have 9 to 60 carbon atoms, may be the same or different. Furthermore, the structure thereof is selected from among straight chain, branched, and partially branched. In the present invention, it is particularly preferable for $R^2$ to be an unsubstituted straight chain monovalent hydrocarbon group. An unsubstituted monovalent hydrocarbon group can be, for example, an alkyl group, aryl group, or aralkyl group having 9 to 60 carbon atoms, preferably 9 to 30 carbon atoms, and more preferably 10 to 25 carbon atoms. On the other hand, examples of the substituted monovalent hydrocarbon group include perfluoroalkyl groups, aminoalkyl groups, amide alkyl groups, and carbinol groups having from 9 to 30 carbons, preferably from 9 to 30 carbons, and more preferably from 10 to 24 carbons. Additionally, the carbon atoms of the monovalent hydrocarbon groups may be partially substituted with alkoxy groups, and examples of these alkoxy groups include methoxy groups, ethoxy groups, and propoxy groups. This type of monovalent hydrocarbon group is particularly preferably an alkyl group having 9 to 30 carbon atoms, and an example thereof is a group represented by the general formula —$(CH_2)_v$—$CH_3$ (v is a number in a range of 8 to 29). Particularly, an alkyl group having 10 to 24 carbon atoms is preferable.

The chain organosiloxane group in general formula (2-1) or (2-2) has a straight chain polysiloxane chain structure, unlike a silylalkyl group, which has a siloxane dendron structure. In general formula (2-1) or (2-2), $R^{11}$ are each independently a substituted or unsubstituted monovalent hydrocarbon group having from 1 to 30 carbon atoms, a hydroxyl group, or a hydrogen atom. The substituted or unsubstituted monovalent hydrocarbon group with 1 to 30 carbon atoms is preferably an alkyl group with 1 to 30 carbon atoms, an aryl group with 6 to 30 carbon atoms, and is exemplified by a methyl group, ethyl group, propyl group, butyl group, pentyl group, hexyl group, heptyl group, octyl group, decyl group, or other alkyl group; a cyclopentyl group, cyclohexyl group, or other cycloalkyl group; or a phenyl group, tolyl group, or other aryl group. The hydrogen atoms bonded to the carbon atoms of these groups may be substituted at least partially by fluorine or a similar halogen atom, or an organic group containing an epoxy group, acyl group, carboxyl group, amino group, methacryl group, mercapto group, or the like. A methyl group, a phenyl group, or a hydroxyl group is particularly preferable as $R^{11}$. A configuration in which a part of $R^{11}$ is a methyl group and another part of $R^{11}$ is a long chain alkyl group having 8 to 30 carbon atoms is also preferable.

In general formula (2-1) or (2-2), t is a number in a range from 2 to 10; r is a number in a range from 1 to 500; and r preferably is a number in a range from 2 to 500. Such a straight chain organosiloxane group is hydrophobic. From the standpoint of compatibility with various oil agents, r preferably is a number in a range from 1 to 100, and particularly preferably is a number in a range from 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external use preparation or cosmetic composition that incorporates the glycerin derivative-modified silicone is used, the silylalkyl group inhibits an unpleasant sticky feeling, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the substituted or unsubstituted, straight or branched monovalent hydrocarbon group having 1 to 30 carbon atoms (the $R^3$ moieties in general formula (3)) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbons is from 1 to 30).

Among the phenyl group or the alkyl group having from 1 to 6 carbons represented by $R^4$ in general formula (3), examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups.

In the aforementioned general formula (3), in the case of i=k, $R^4$ is preferably a methyl group or a phenyl group. In particular, $R^4$ is preferably a methyl group when i=k.

From a technical standpoint, the number of generations k is preferably an integer from 1 to 3, and more preferably is 1 or 2. In each of the number of generations, the group represented by $L^1$ is represented as follows. In the formulae, $R^3$, $R^4$, and Z are the same groups as described above.

When the number of generations is k=1, $L^1$ is expressed by the following general formula (3-1).

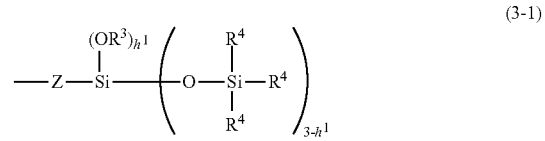

(3-1)

When the number of generations is k=2, $L^1$ is expressed by the following general formula (3-2).

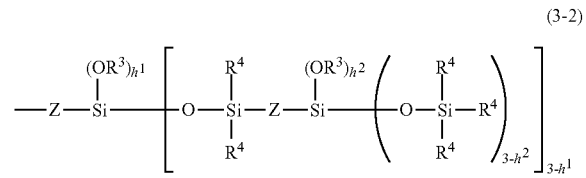

(3-2)

When the number of generations is k=3, $L^1$ is expressed by the following general formula (3-3).

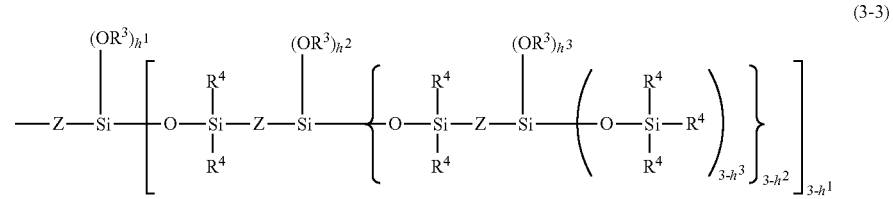

(3-3)

In the structures expressed by the general formulae (3-1) to (3-3) in the case of the number of generations is from 1 to 3, each of $h^1$, $h^2$ and $h^3$ moieties is independently a number in a range from 0 to 3. These $h^i$ moieties are preferably a number in a range from 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups expressed by the following general formula.

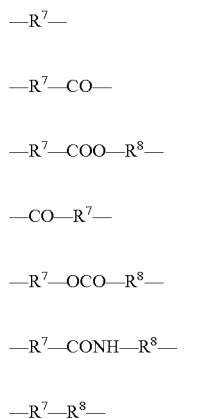

Of these, Z in $L^1$ is preferably a divalent organic group expressed by general formula —$R^7$— that is introduced by a reaction between a silicon-bonded hydrogen atom and an alkenyl group. Likewise, Z is preferably a divalent organic group expressed by general formula —$R^7$—COO—$R^8$— that is introduced by a reaction between a silicon-bonded hydrogen atom and an unsaturated carboxylic ester group.

On the other hand, in the silylalkyl group represented by $L^i$, in which the number of generations k is 2 or more, and $L^i$ is $L^2$ to $L^k$, Z is preferably an alkylene group having 2 to 10 carbons and, in particular, is preferably a group selected from an ethylene group, a propylene group, a methylethylene group, and a hexylene group, and most preferably is an ethylene group.

In the general formula described above, $R^7$ are each independently a substituted or unsubstituted straight or branched chain alkylene group or alkenylene group having from 2 to 22 carbons or an arylene group having from 6 to 22 carbons. More specifically, examples of $R^7$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^7$ is preferably a group selected from an ethylene group, a propylene group, a methylethylene group, and a hexylene group.

In the general formula described above, $R^8$ is a group selected from divalent organic groups expressed by the following formula.

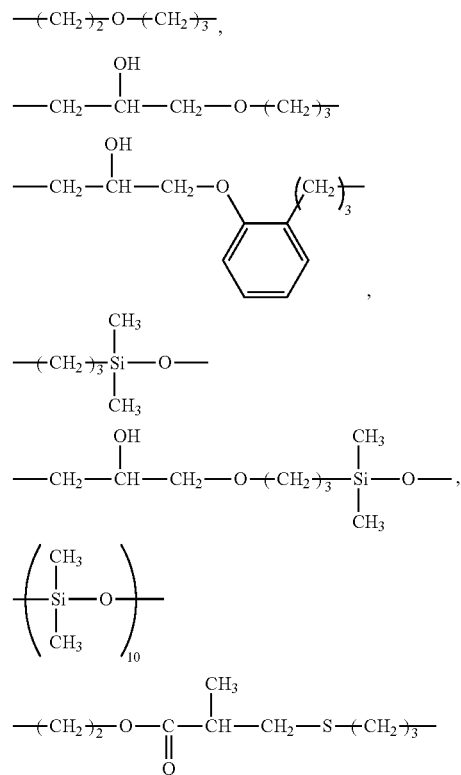

In general formula (1), Q is a glycerin derivative group-containing organic group, and forms the hydrophilic site of the aforementioned glycerin derivative-modified silicone. The structure of Q is not limited provided that the structure has a glycerin derivative site, but the glycerin derivative residue is preferably bonded to the silicon atom via a divalent organic group.

Here, "glycerin derivative residue" refers to a hydrophilic group having a (poly)glycerin structure, and refers to a hydrophilic group having a monoglycerin, a diglycerin, a triglycerin, a tetraglycerin, and at least a pentaglycerin structure. Additionally, the terminal hydroxyl group may be partially capped with an alkyl group. Furthermore, the (poly)glycerin structure may be straight or branched, and may be a structure that is branched in a dendritic manner as well.

The glycerin derivative group-containing organic group (Q) described above is preferably bonded to a silicon atom via a linking group that is at least divalent and is preferably a glycerin derivative group-containing organic group comprising at least one type of hydrophilic unit selected from hydrophilic units represented by structural formulae (3-3) to (3-5) below.

-continued (3-4)
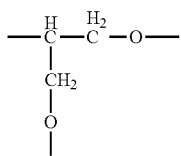

(3-5)
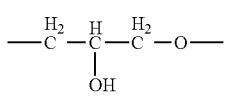

In formulae (3-3) to (3-5), W is a hydrogen atom or an alkyl group having from 1 to 20 carbons, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units represented by structural formulae (3-3) to (3-5) are hydrophilic units included in a hydrophilic group derived from a hydrophilic compound selected principally from polyhydric alcohols including glycerin, polyglycerins (also called "polyglycerols"), and polyglycidyl ethers or compounds in which terminal hydroxyl groups thereof are partially capped by hydrocarbon groups. Furthermore, note that the glycerin derivative group-containing organic group (Q) according to the present invention may be a hydrophilic group optionally comprising a hydrophilic structure (polyether structure) including an oxyalkylene unit expressed by —$C_rH_{2r}O$— (e.g. an oxyethylene unit or an oxypropylene unit).

In the general formula (1), Q may be, for example, a hydrophilic group that does not have a branched structure such as a monoglycerin-modified group or a diglycerin-modified group, and may also be a hydrophilic group that has a partial branched structure in the functional group such as a polyglycerol group or a polyglycidylether group.

More specifically, Q may be a hydrophilic segment bonded to the silicon atom via a linking group that is at least divalent, comprising at least one linearly bonded hydrophilic unit selected from hydrophilic units represented by the following structural formulae (3-3) to (3-5). Similarly, Q may be a hydrophilic segment bonded to the silicon atom via a linking group that is at least divalent, comprising not less than two of at least one hydrophilic unit selected from hydrophilic units represented by structural formulae (3-3) to (3-5) above, and a branch unit selected from groups represented by structural formulae (3-6) to (3-8) below.

(3-6)
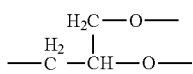

(3-7)
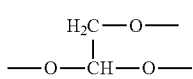

(3-8)
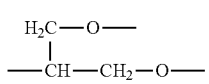

In structural formulae (3-6) to (3-8), the at least one hydrophilic unit selected from the hydrophilic units expressed by the general formulae (3-3) to (3-5) are each independently bonded to the two oxygen atoms. The hydrophilic unit may further be bonded to a branch unit selected from groups represented by structural formulae (3-6) to (3-8). Moreover, the hydrophilic unit may be formed so as to have a dendroid-shape polyether structure, a polyglyderol structure, or a polyglycidyl ether structure obtained by branching into multiple generations. For example, the structure of a hydrophilic group Q which has one branch unit represented by structural formula (3-6) and two branch units represented by structural formula (3-8) and which is branched in a dendritic manner is shown below, but it goes without saying that dendroid-shape polyglycerol structures are not limited to this example.

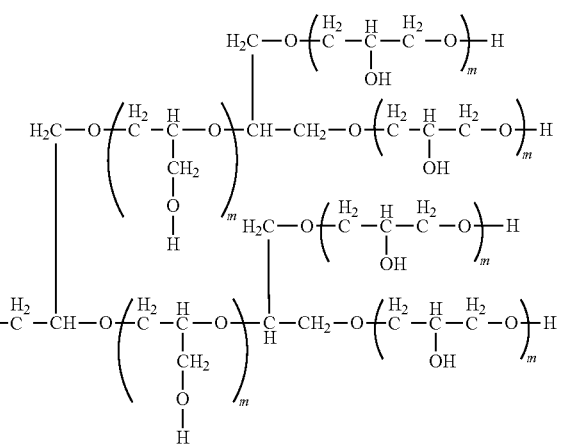

(In the formula, m is a number in a range from 0 to 50, provided that not all of the m moieties are 0).

The linking group that is at least divalent is a bonding site with respect to the silicon atom included in the hydrophilic group (Q), and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

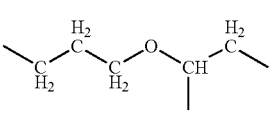

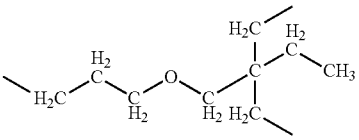

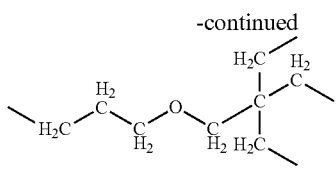
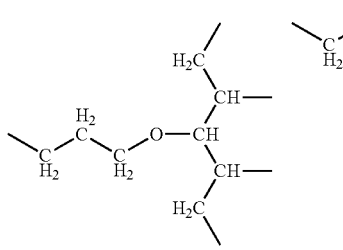
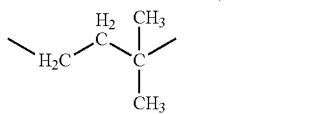
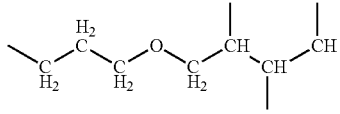
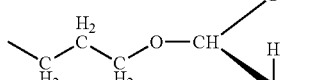

More preferably, Q is a hydrophilic group represented by structural formulae (4-1) to (4-4) below, and these are generally hydrophilic groups derived from polyglycerin-based compounds.

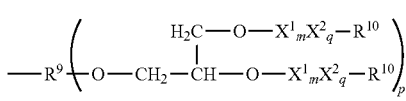 (4-1)

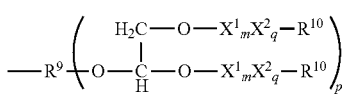 (4-2)

(4-3)

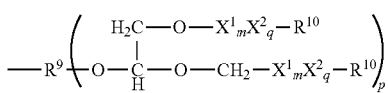 (4-4)

In formulae (4-1) to (4-4), $R^9$ is an organic group having (p+1) valence, and p is a number that is greater than or equal to 1 and less than or equal to 3. As the aforementioned $R^9$, the same groups as the aforementioned linking groups having two or more valences may be mentioned.

It is more preferable that p is equal to 1 and that $R^9$ is a group selected from divalent organic groups expressed by the following general formulae.

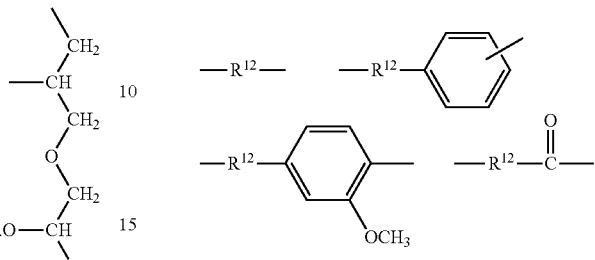

In the formulae, $R^{12}$ may have a substituent, and are each independently a straight or branched chain alkylene group or alkenylene group having from 2 to 22 carbons, or an arylene group having from 6 to 22 carbons.

$X^1$ are each independently at least one hydrophilic unit selected from the hydrophilic units expressed by general formulae (3-3-1) to (3-5-1) below, and m is a number in a range of 1 to 5, and is more preferably a number in a range of 1 to 4.

 (3-3-1)

 (3-4-1)

 (3-5-1)

$X^2$ is an optional oxyalkylene unit that Q may comprise, and q is a number in a range from 0 to 50. In the present invention, Q is a glycerin derivative group-containing organic group, and q is preferably a number in a range from 0 to 30, and is preferably 0.

Note that $X^2$ is preferably an oxyethylene unit or oxypropylene unit. Additionally, when $X^2$ is continuously bonded, at least one type of polyoxyalkylene unit expressed by $-(C_2H_4O)_{t1}(C_3H_6O)_{t2}-$ (wherein, t1 and t2 are each a number not less than 0, and (t1+t2) is a number in a range from 0 to 50 and preferably a number in a range from 0 to 30) can be included in Q.

Here, the manner in which $X^1$ and $X^2$ are bonded can be block or random. That is, the hydrophilic group Q may be a hydrophilic group in which hydrophilic segments, which are obtained by bonding hydrophilic units expressed by general formulae (3-3-1) to (3-5-1) above in a block manner, are bonded to hydrophilic segments comprising polyoxyalkylene units, and may be a hydrophilic group in which these constituent units are bonded in a random manner. An example thereof is a bonding pattern such as —$(X^2)_{m1}$—$X^1$—$(X^2)_{m2}$—$X^1$—.

$R^{10}$ is a hydrogen atom or a group selected from the group consisting of glycidyl groups, acyl groups, and alkyl groups having from 1 to 20 carbons.

From the perspectives of gel formability and thickening effect with respect to the oil agent component of the glycerin derivative-modified silicone of the present invention, a particularly preferable hydrophilic group Q is the (poly) glycerin derived hydrophilic group represented by the following structural formula (4-1-1).

(4-1-1)

In the formula, $R^{9'}$ is a divalent organic group, and can be a group synonymous with those mentioned above. $X^1$ and $R^{10}$ are synonymous with the groups described above, and m is a number in a range of 1 to 5.

In the glycerin derivative-modified silicone of the present invention, from the perspectives of thickening effect and gel formability with respect to the oil agent component, use as a surfactant (emulsifier) or various treatment agents (powder dispersing agent or surface treatment agent), and particularly use as a powder treatment agent and a cosmetic composition raw material, the hydrophilic group Q is a hydrophilic group derived from a (poly)glycerin system compound and is most preferably a hydrophilic group derived from (poly)glycerin. Specifically, the hydrophilic group Q is a (poly)glycerin-monoallyl ether or a (poly)glyceryl eugenol, which are examples of hydrophilic groups derived from (poly)glycerin compounds having a monoglycerin, diglycerin, triglycerin, or tetraglycerin structure.

The bond position of the glycerin derivative group-containing organic group can be either the terminal or side chain of polysiloxane, which is the main chain; and the structure may have two or more glycerin derivative group-containing organic groups per molecule of glycerin derivative-modified silicone. Furthermore, the two or more glycerin derivative group-containing organic groups can be the same or different glycerin derivative group-containing organic groups. These two or more glycerin derivative group-containing organic groups can be structured such that bonding occurs only in a side chain of polysiloxane, which is the main chain, only at a terminal, or in a side chain and at a terminal.

For the glycerin derivative-modified silicone that is expressed by general formula (1) and that has a glycerin derivative group-containing organic group (-Q), the polysiloxane main chain can be straight, branched, or reticulated (including slightly cross linked and elastomeric). It is particularly advantageous that, in the production method of the present invention, odors can be reduced simply, not only for a glycerin derivative-modified silicone that is liquid and has a low viscosity, but also for a glycerin derivative-modified silicone that is highly viscous to solid (having plasticity, and including a gummy state lacking fluidity), which makes hydrogenation treatment difficult.

The particularly preferable glycerin derivative-modified silicone of the present invention is a glycerin derivative-modified silicone having a straight chain polysiloxane structure represented by structural formula (1-1) below:

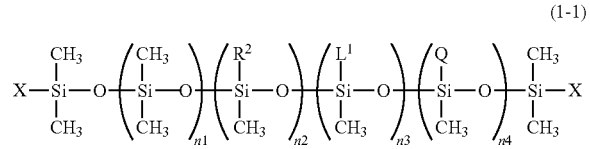
(1-1)

(In the formula, $R^2$, $L^1$, and Q are each independently synonymous with those described above;

X is a group selected from among the groups comprising a methyl group, $R^2$, $L^1$, and Q;

n1, n2, n3, and n4 are each independently a number in a range from 0 to 2,000, and n1+n2+n3+n4 is a number in a range from 0 to 2,000; however, when n4=0, at least one X is Q.)

In formula (1-1), (n1+n2+n3+n4) preferably is a number in a range from 10 to 2,000, more preferably is in a range from 25 to 1,500, and particularly preferably is a number in a range from 50 to 1,000. n1 preferably is a number in a range from 10 to 2,000, more preferably is in a range from 25 to 1,500, and particularly preferably is in a range from 50 to 1,000. n2 preferably is a number in a range from 0 to 250, more preferably in a range from 0 to 150.

When $R^2$ is the aforementioned long chain alkyl group, n2>1 is particularly preferable from the standpoint of compatibility with oil agents other than silicone and surface activity. n3 preferably is a number in a range from 0 to 250, and it is particularly preferable that 3>1, and that it has least one silylalkyl group (-$L^1$) having a siloxane dendron structure in a side chain portion.[1] n4 is a number in a range from 0 to 100, and preferably is in a range from 0 to 50. However, when n4=0, at least one X must be Q.

In the aforementioned structural formula (1-1), it is preferable that Q are each independently a glycerin derivative group-containing organic group expressed by any of general formulae (4-1) through (4-4). In the glycerin derivative-modified silicone, all Qs can be one type of glycerin derivative group-containing organic group, that is expressed by any of general formulae (4-1) through (4-4). A part of the Qs in a molecule can be a glycerin derivative group-containing organic group expressed by any of general formulae (4-1) through (4-4) above. The remaining Qs may be another glycerin derivative group-containing organic group.

Furthermore, the glycerin derivative-modified silicone can be a mixture of one or two or more types of a glycerin derivative-modified silicone expressed by general formula (1). More specifically, the glycerin derivative-modified silicone can be a mixture of at least two types of glycerin derivative-modified silicone, with different types of modified groups, modification rate, and degree of polymerization of the siloxane main chain.

As the aforementioned glycerin derivative-modified silicone, the glycerin derivative-modified silicone represented by the following structural formula (1-1-1) is preferable:

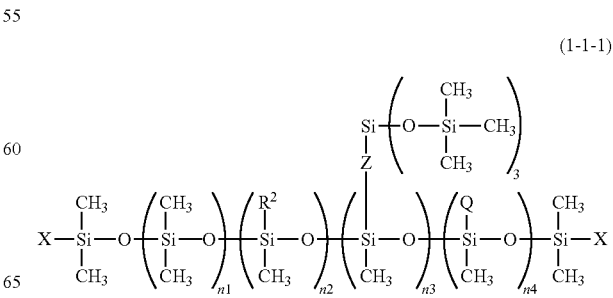
(1-1-1)

(In the formula, $R^2$, Q, X, Z, n1, n2, n3, and n4 are synonymous with those described above), or the following structural formula (1-1-2):

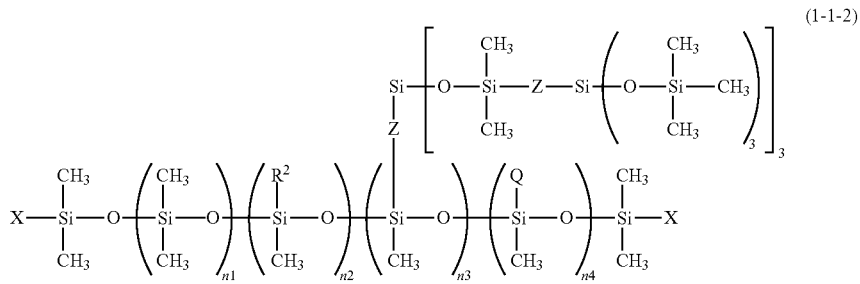

(In the formula, $R^2$, Q, X, Z, n1, n2, n3, and n4 are synonymous with those described above).

The modification rate of organopolysiloxane due to the glycerin derivative group-containing organic group is preferably in a range from 0.001 to 50 mol %, more preferably within the range from 0.01 to 30 mol %, and yet more preferably within the range from 0.1 to 10 mol % of all functional groups bonded to polysiloxane, which is the main chain. Furthermore, in the glycerin derivative-modified silicone represented by structural formula (1-1), the modification rate (mol %) resulting from the glycerin derivative group-containing organic group is expressed by the following formula:

Modification rate (mol %)=(number of glycerin derivative group-containing organic groups bonded to silicon atoms per molecule)/(6+2×(n1+n2+n3+n4))×100

For example, in the case of a glycerin derivative-modified silicone comprising trisiloxane having one glycerin derivative group-containing organic group, of the 8 silicon atom bonded functional groups, one is modified by the glycerin derivative group-containing organic group, so the modification rate by the glycerin derivative group-containing organic group is 12.5 mol %.

(Synthesis Reaction for a Glycerin Derivative-modified Silicone or a Composition Comprising the Same)

The glycerin derivative-modified silicone can be obtained by, for example, reacting (a1) a glycerin derivative having one reactive unsaturated group per molecule, (b1) organopolysiloxane having silicon atom bonded hydrogen atoms, and (c1) an organic compound having one reactive unsaturated group per molecule, and if necessary, (d1) a siloxane dendron compound having one reactive unsaturated group per molecule, and/or (e1) a long chain hydrocarbon compound or a chain organopolysiloxane compound having one reactive unsaturated group per molecule in the presence of a hydrosilylation reaction catalyst. The reactive unsaturated group preferably is an unsaturated functional group having a carbon-carbon double bond, and is exemplified by an alkenyl group or unsaturated fatty acid ester group. The —$R^1$ is introduced by component (c1), the -$L^1$ is introduced by component (d1), and the id —$R^2$ is introduced by component (e1). Furthermore, at this time, by using an excessive amount of component (a1) for the silicon atom bonded hydrogen atoms in component (b1), it is possible to obtain a composition comprising a glycerin derivative-modified silicone and component (a1).

More specifically, a glycerin derivative-modified silicone can be obtained as below, for example.

The glycerin derivative-modified silicone can be obtained by addition reacting with organopolysiloxane having a silicon-hydrogen bond, an unsaturated organic compound having a carbon-carbon double bond at one terminal of the molecular chain, and an unsaturated ether compound of a glycerin derivative having a carbon-carbon double bond in the molecule. Furthermore, a siloxane dendron compound having a carbon-carbon double bond at one terminal of the molecular chain, and/or an unsaturated long chain hydrocarbon compound having a carbon-carbon double bond at one terminal of the molecular chain, or a chain organopolysiloxane having a carbon-carbon double bond at one terminal of the molecular chain can be further addition reacted.

In the above case, the glycerin derivative-modified silicone can be obtained as the product of a hydrosilylation reaction between the unsaturated organic compound and the glycerin derivative unsaturated ether compound, and arbitrarily the siloxane dendron compound and/or an unsaturated long chain hydrocarbon compound, or a chain organopolysiloxane having a carbon-carbon double bond at one terminal of the molecular chain and a SiH group-containing siloxane. This enables the introduction of an organic group and a glycerin derivative group-containing organic group, and arbitrarily a silylalkyl group having a siloxane dendron structure and/or a long chain hydrocarbon group or a chain organopolysiloxane group into the polysiloxane chain of the glycerin derivative-modified silicone. This reaction can be performed as a batch or can take the form of successive reactions. However, successive reactions are preferable from the perspectives of safety and quality control.

For example, the glycerin derivative-modified silicone can be obtained by reacting at least the (b2) organohydrogensiloxane expressed by the following formula (1') and (a2) a glycerin derivative having one reactive unsaturated group per molecule, in the presence of a hydrosilylation reaction catalyst.

$$R^1{}_aH_{b+c+d}SiO_{(4-a-b-c-d)/2} \quad (1')$$

(In the formula, $R^1$, a, b, c, and d are synonymous with those described above) It is preferable to further react (d) a siloxane dendron compound having one reactive unsaturated group per molecule, and/or (e) a hydrocarbon compound having one reactive unsaturated group per molecule, or chain organopolysiloxane having one reactive unsaturated group per molecule.

The glycerin derivative-modified silicone can be preferably produced by reacting together component (a2), component (d) and/or component (e), as well as (b2) the organohydrogensiloxane expressed by general formula (1'), or by successively addition reacting the (b2) organohydrogensiloxane and arbitrarily the component (d), and/or the component (e), and further addition reacting the component (a2), in the state where (a2) a glycerin derivative having one reactive unsaturated group per molecule, and arbitrarily (d) a siloxane dendron compound having one reactive unsaturated group per molecule, and/or (e) a hydrocarbon compound having one reactive unsaturated group per molecule or a chain organopolysiloxane having one reactive unsaturated group per molecule coexist.

As (b2) an organohydrogensiloxane used in the synthesis of the glycerin derivative-modified silicone, the organohydrogensiloxane is preferably represented by, for example, the following structural formula (1-1)':

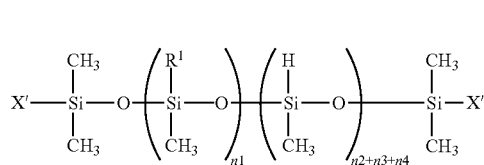

(1-1)'

(In the formula, $R^1$ are each independently synonymous with that described above;
X' is a group selected from $R^1$ or hydrogen atom; and
n1, n2, n3, and n4 are synonymous with those described above; however, when n2+n3+n4=0, at least one X' is a hydrogen atom)

The glycerin derivative-modified silicone is preferably synthesized by subjecting to a hydrosilylation reaction (a) a glycerin derivative having a carbon-carbon double bond at a terminal of the molecular chain, and (b) an organohydrogenpolysiloxane; and the organohydrogensiloxane (component (b)) is preferably the organohydrogensiloxane obtained by successively addition reacting the component (d1) and/or the component (e1). In this case, the organohydrogensiloxane immediately prior to reaction with component (a) (after successive reactions with other components) is preferably represented by the following structural formula (1-1A).

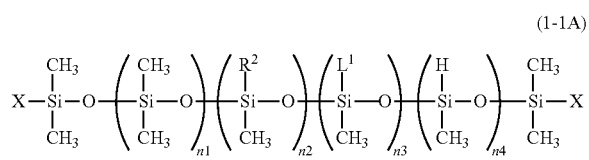

(1-1A)

(In the formula,
$R^2$ and $L^1$ are each independently synonymous with those described above;
X is selected from the groups comprising a methyl group, $R^2$, $L^1$, and a hydrogen atom (H);
n1, n2, n3, and n4 are each independently a number in a range from 0 to 2,000, and
n1+n2+n3+n4 is a number in a range from 0 to 2,000; however, when n4=0, at least one X is a hydrogen atom.)

A glycerin derivative having one reactive unsaturated group per molecule, which is used in the synthesis of the glycerin derivative-modified silicone, is preferably (a) a glycerin derivative having a carbon-carbon double bond at the terminal of molecular chain. This is a (poly)glycerin derivative having an allyl(poly)glycerin, allyl polyglycidyl ether, (poly)glycerin monoallyl ether, or similar reactive functional group having an alkenyl group or the like at the molecular terminal, and can be synthesized according to a known method.

In the glycerin derivative-modified silicone of the present invention, from the perspectives of thickening effect and gel formability with respect to an oil agent, use as a surfactant (emulsifier), various treatment agents (powder dispersing agents or surface treatment agents), and particularly use as a powder treatment agent and a cosmetic composition raw material, component (a) is specifically a (poly)glycerin monoallyl ether or a (poly)glyceryl eugenol, of which examples are (poly)glycerin compounds having a monoglycerin, a diglycerin, a triglycerin, or a tetraglycerin structure.

Such a component (a) can be exemplified by a glycerin derivative having a carbon-carbon double bond at the terminals of the molecular chain shown by the following structural formulae (4-1') through (4-4'). In the formulae, $X^1$, $X^2$, and $R^{10}$ are groups synonymous with the groups described above, and m and q are numbers synonymous with the numbers described above. R' is an unsaturated organic group having a carbon-carbon double bond at the terminal, and is preferably a substituted or unsubstituted, straight or branched unsaturated hydrocarbon group having 3 to 5 carbon atoms. Examples of the unsaturated hydrocarbon group having from 3 to 5 carbon atoms include allyl groups, butenyl groups, methallyl groups, and similar alkenyl groups; and the unsaturated hydrocarbon group is preferably an allyl group.

(4-1')

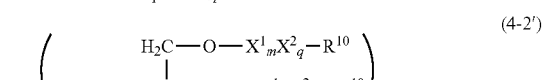

(4-2')

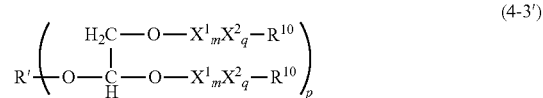

(4-3')

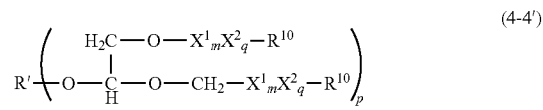

(4-4')

(d) The siloxane dendron compound that has one reactive unsaturated group per molecule used in the synthesis of a glycerin derivative-modified silicone of the present invention, is preferably a compound having a siloxane dendron structure with one carbon-carbon double bond at a molecular terminal, and is expressed by the following general formula (3'):

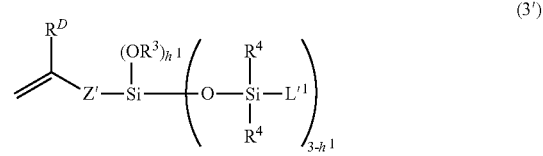

(3')

(In the formula,
$R^3$ and $R^4$ are synonymous with those described above, $R^D$ is a hydrogen atom or a methyl group;
Z' is a divalent organic group;
$h^1$ is a number in a range from 0 to 3;

$L'^1$ is the $R^4$ moiety or, when j=1, a silylalkyl group expressed by general formula (3″) below:

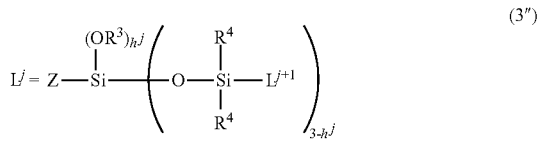

(wherein $R^3$ and $R^4$ are synonymous with those described above;

Z is a divalent organic group;

j indicates the number of generations of the silylalkyl group that is represented by $L^j$, when the number of generations (the number of repetitions) of the silylalkyl group is k', j is an integer of 1 to k', and the number of generations k' is an integer from 1 to 9; $L^{j+1}$ is the silylalkyl group when j is less than k' and is the $R^4$ moiety when j=k'; and $h^j$ is a number in a range from 0 to 3).

(e) The hydrocarbon compound having one reactive unsaturated group per molecule or chain organopolysiloxane having one reactive unsaturated group per molecule used in the synthesis of a glycerin derivative-modified silicone of the present invention, is preferably a mono unsaturated organic compound expressed by the following general formula (2'):

(wherein R' is synonymous with that described above; and $R^{2'}$ represents a substituted or unsubstituted, straight or branched monovalent hydrocarbon group having 7 to 58 carbon atoms) or the following general formula (2-1):

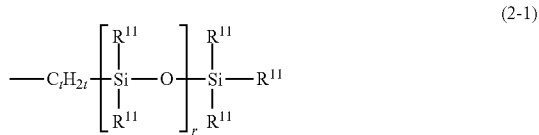

(wherein $R^{11}$, t, and r are synonymous with those described above); or the following general formula (2-2):

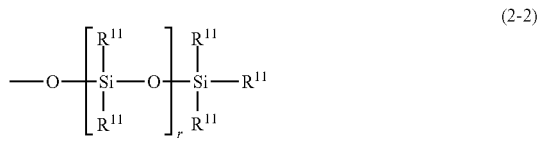

(wherein $R^{11}$ and r are synonymous with those described above).

The hydrocarbon compound having one reactive unsaturated group in the molecule (e) is preferably a monounsaturated hydrocarbons having from 9 to 30 carbons and is more preferably a 1-alkene. Examples of the 1-alkene include 1-nonene, 1-decene, 1-undecene, 1-dodecene, 1-tridecene, 1-tetradecene, 1-hexadecene, 1-octadecene and the like. Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

The hydrosilylation reaction used to synthesize the glycerin derivative-modified silicone or the composition thereof can be carried out using a publicly known method in the presence or absence of a solvent. Here, the reaction solvent can be an alcoholic solvent such as ethanol and isopropyl alcohol, an aromatic hydrocarbon-based solvent such as toluene and xylene; an ether-based solvent such as dioxane and THF; an aliphatic hydrocarbon-based solvent such as n-hexane, cyclohexane, n-heptane, cycloheptane and methylcyclohexane; or a chlorinated hydrocarbon-based organic solvent such as carbon tetrachloride.

The hydrosilylation reaction may be performed in the presence or absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, and the like; and a platinum complex such as platinum-vinylsiloxane complex, platinum phosphine complex, platinum-phosphite complex, platinum alcoholate catalyst, and the like. If a platinum catalyst is used, the usage quantity of the solvent is approximately 0.0001 to 0.1 wt. %, and preferably 0.0005 to 0.05 wt. % in terms of platinum metal, but is not particularly limited.

A reaction temperature of the hydrosilylation reaction is typically from 30 to 120° C., and a reaction time is typically from 10 minutes to 24 hours and preferably from 1 to 10 hours.

When the hydrosilylation reaction is performed, the ratio [amount of substance of carbon-carbon double bonds in glycerin derivative group-containing compound/amount of substance of silicon-bonded hydrogen atoms to be added to the carbon-carbon double bonds of the glycerin derivative group-containing compound in the organohydrogenpolysiloxane] is preferably in a range from 0.8 to 1.5, and more preferably in a range from 1.0 to 1.3. That is, when synthesizing a glycerin derivative-modified silicone or a glycerin derivative-modified silicone-containing composition of the present invention, it is more preferable to use a slight excess of glycerin derivative group-containing compound. Although processing with the ratio above 1.5 is also possible, the proportion of residual raw material increases, so it is not economical. Furthermore, when the ratio is in a range from 0.8 to 1.0, the amount of the silicon-bonded hydrogen atoms consumed by the hydrosilylation reaction falls into the range from 0.8 to 1.0, and silicon-bonded hydrogen atoms remain at the ratio of 0 to 0.2. However, it is possible to cause dehydrogenation reactions with hydroxyl groups contained in the glycerin derivative group and alcoholic hydroxyl groups of the reaction solvent, which can consume the remaining silicon-bonded hydrogen atoms, depending on the reaction conditions.

On the other hand, if the ratio is less than 0.8, there is a risk that unreacted organohydrogenpolysiloxane will remain. When such a glycerin derivative-modified silicone or a glycerin derivative-modified silicone-containing composition is used as the raw material for an external use preparation or a cosmetic composition, residual organohydrogenpolysiloxane might react with the other raw materials, and generate hydrogen gas. This might cause such undesirable effects as alteration of the external use preparation or the cosmetic composition at the incorporation destination, fire, container expansion, and the like. In addition, when an attempt is made to consume the remaining silicon-bonded hydrogen atoms by a dehydrogenation reaction when the ratio is less than 0.8, the proportion of Si—O—C crosslinked bonds increases, which increases the tendency to cause gelation during production. Therefore, to enable the complete and safe consumption of organohydrogenpolysiloxane, it is preferable that the ratio exceeds 0.8, i.e., that 0.8 equivalent or more of the glycerin derivative group-containing compound is reacted.

(Acidizing and Odor Reduction of a Glycerin Derivative-modified Silicone or a Composition Comprising the Same)

The method of producing a glycerin derivative-modified silicone or a composition comprising the same of the present invention is characterized by including a process that treats a glycerin derivative-modified silicone or a composition comprising the same with one or more type of acidic inorganic salt, which is solid at 25° C. and water soluble, and which is such that a pH at 25° C. of an aqueous solution prepared by dissolving 50 g of the acidic inorganic salt in 1 L of ion exchanged water is 4 or lower, thereby considerably reducing the odor thereof. As a result, the production method of the present invention has an aspect as "an odor reduction method."

The acidic inorganic salt used for the above acidizing is a characteristic compound of the present invention. By using such an acidic inorganic salt to treat a glycerin derivative-modified silicone or a composition comprising the same, it is possible to implement much more effective odor reduction than that of the normal acidic substance based treatment.

The glycerin derivative-modified silicone or composition comprising the same processed by the production method of the present invention can be synthesized by the above method. The production method of the present invention is preferably a method of producing a glycerin derivative-modified silicone or a composition comprising the same, that includes a process [A] that synthesizes a glycerin derivative-modified silicone or a composition comprising the same by subjecting to a hydrosilylation reaction (a) a glycerin derivative having a carbon-carbon double bond at the terminal of a molecular chain, and (b) an organohydrogenpolysiloxane; and, a process [B] that, together with synthesis process [A] or after synthesis process [A], treats glycerin derivative-modified silicone or a composition comprising the same in the presence of at least one type of (c) acidic inorganic salt, characterized by the acidic inorganic salt being solid at 25° C. and water soluble, and a pH at 25° C. of an aqueous solution prepared by dissolving 50 g of the acidic inorganic salt in 1 L of ion exchanged water being 4 or lower. In addition, because a treatment process that uses the acidic inorganic salt involves the generation of odor-causing substances, it is more preferable to include a process that removes odor-causing substances by heating or depressurizing, from the perspective of odor reduction effectiveness.

For example, in process [A], when the hydrosilylation reaction is performed using (a) a glycerin derivative compound such as (poly)glycerin monoallylether and the like, and (b) the straight chain organohydrogenpolysiloxane represented by the structural formula (1-1A), with an excessive amount of substance of component (a) relative to the silicon-bonded hydrogen atoms in component (b), the glycerin derivative-modified silicone represented by structural formula (1-1) is synthesized, and it is possible to obtain the crude product of the glycerin derivative-modified polysiloxane composition of the present invention, which contains the glycerin derivative-modified silicone and unreacted component (a).

<Process (B)>

Process [B] is a process that characterizes a method of producing a low odor glycerin derivative-modified polysiloxane composition of the present invention, and is an essential process for efficiently reducing the odors of the composition and effectively suppressing the generation of odors over time by hydrolyzing the composition using specific acidic inorganic salts, with practically no breakage of the silicon-oxygen bonds forming the main chain of polysiloxane or the carbon-oxygen bonds of side chain portions.

Such a process [B] specifically removes odor-causing substances from the crude products of a glycerin derivative-modified polysiloxane composition by using hydrolysis, and it is characterized by treating in the presence of at least one type of acidic inorganic salt, which is solid at 25° C. and water soluble, and a pH at 25° C. of an aqueous solution prepared by dissolving 50 g of the acidic inorganic salt in 1 L of ion exchanged water is 4 or lower. Note that pH values in the present invention are values that are measured using a pH meter having a glass electrode in a sample aqueous solution at room temperature (25° C.). In the present application, HM-10P produced by DKK-TOA Corporation was used for the pH measurement.

The acidic inorganic salt (component (c)) must be a solid at 25° C., must be water soluble, and the aqueous solution must have a pH of less than or equal to 4 when 50 g of the acidic inorganic salt is dissolved in 1 L of ion exchanged water. More preferably, the pH is at most 3.5, and particularly preferably the pH is at most 2.0. By using such a water soluble acidic inorganic salt for hydrolysis treatment of the composition, it is possible to reduce odors in the composition highly effectively and suppress odorization over time effectively, with almost no breakage of carbon-oxygen bonds or silicon-oxygen bonds.

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, and the like.

More specifically, the component (c) is preferably at least one type of acidic inorganic salt comprising a hydrogensulfate ion ($HSO_4^-$) or a hydrogensulfite ion ($HSO_3^-$) and a monovalent cation ($M^+$). Examples of the monovalent cation ($M^+$) include alkali metal ions or an ammonium ion. Particularly, the monovalent cation is preferably at least one type selected from the group consisting of a sodium ion, a potassium ion, and an ammonium ion. Additionally, one type of the acidic inorganic salt may be used alone or two or more types of acidic inorganic salt may be used. Furthermore, the acidic inorganic salt can be easily removed via filtration because the acidic inorganic salt is solid at room temperature (25° C.). Additionally, because it is water soluble, the acidic inorganic salt can be easily rinsed off using water, even in the cleaning process after production.

On the other hand, in hydrolysis treatment based on an acetic acid salt, phosphoric acid salt, and the like that does not satisfy the conditions of the component (c), it is impossible to sufficiently reduce the odor of the composition after hydrolysis. On the other hand, in hydrolysis treatment based on a strong acid such as hydrochloric acid and the like, and in hydrolysis treatment based on a publicly known solid acid of zirconium sulfate and the like, the odor can be reduced by a certain amount, but carbon-oxygen bonds and silicon-oxygen bonds of the composition break easily after the hydrolysis.

Specific examples of the acidic inorganic salt, which is component (c), are lithium hydrogensulfate, sodium hydrogensulfate, potassium hydrogensulfate, rubidium hydrogensulfate, cesium hydrogensulfate, ammonium hydrogensulfate, sodium hydrogensulfite, or hydrates thereof. The pH of aqueous solutions in which 50 g of the acidic inorganic salt is dissolved in 1 L of ion exchanged water is as shown in Table below. From the perspective of the technical benefit of reducing odor, the water soluble acidic inorganic salt having a pH of not higher than 2.0 is preferably at least one type of acidic inorganic salt selected from the group consisting of sodium hydrogensulfate, potassium hydrogensulfate, and ammonium hydrogensulfate.

TABLE 1

| Acidic inorganic salt | pH (50 g/L) |
|---|---|
| Sodium hydrogensulfate | 1.5 or lower |
| Potassium hydrogensulfate | 2.0 or lower |
| Ammonium hydrogensulfate | 1.5 or lower |
| Sodium hydrogensulfite | 3.5 |

For example, treatment in the presence of an acidic inorganic salt, which characterizes the present invention, includes (1) carrying out decomposition treatment by adding the above-mentioned acidic inorganic salt to a reaction system of a glycerin derivative-modified polysiloxane composition synthesized using a hydrosilylation reaction (e.g. in a flask or other reaction container), and then stirring; and (2) carrying out hydrolysis treatment by adding an acidic inorganic salt and water or an acidic inorganic salt, water, and a hydrophilic solvent and then stirring; and the like. The treatment process that uses the acidic inorganic salt is preferably carried out in the presence of water and/or a hydrophilic solvent.

A particularly preferable hydrolysis treatment is a hydrolysis treatment whereby, after the aforementioned process [A], at least an acidic inorganic salt and water are added to a reaction system containing a crude product of the glycerin derivative-modified polysiloxane composition of the present invention, and depending on the case, another hydrophilic solvent is added to improve the treatment efficiency by improving compatibility, and then mechanical force is used to stir. The hydrolysis can be carried out at any temperature and treatment time, and can be carried out at a temperature from 0 to 200° C. and more preferably from 50 to 100° C. for a reaction time of from 0.1 to 24 hours and more preferably from about 0.5 to 10 hours. A used amount of acidic inorganic salt can be appropriately selected according to the treatment apparatus and the treatment time. However, an amount in a range from 100 to 10,000 ppm is preferable for a glycerin derivative-modified polysiloxane composition, and in a range from 500 to 5,000 ppm is more preferable.

In the production method of the present invention, it is preferable to include a stripping process that removes low-boiling components (propionaldehyde, etc.), which are odor-causing substances. In addition, after stripping, it is possible to hydrolyze more of the propenyl ether group-containing glycerin derivative by treating again in the presence of an acidic inorganic salt, and propionaldehyde and the like, which are odor-causing substances, can be removed. At this time, there is an advantage that, because acidic inorganic salt remains, an acidic inorganic salt need not be newly added. Therefore, it is only necessary to add a hydrophilic solvent, typified by water. That is, the aforementioned process [B] and the stripping process can be repeated two times or more, to increase the degree of odor reduction, or the like.

Furthermore, the "materials with a low boiling point" which are distilled off by the stripping process, include not only propionaldehyde which is an odor-causing substance, but also the reaction solvents used in the hydrosilylation reaction (process [A]), the water used in the odor reduction treatment process, hydrophilic solvents, and the like.

The stripping process (the distilling off of materials with a low boiling point) can be performed for crude products of glycerin derivative-modified polysiloxane composition, as pre processing of process [B], and it can be performed for the glycerin derivative-modified polysiloxane composition as post processing of process [B]. In addition, the stripping process can be performed as the pre processing and post processing of process [B]. The stripping process is preferably performed after the process [B], to remove propionaldehyde, which is an odor-causing substance generated by the hydrolysis reaction.

As the removal method, stripping under normal pressure or under reduced pressure is preferable, and stripping at a temperature of 120° C. or lower is preferable. In order to effectively perform the stripping, the stripping is preferably performed under reduced pressure or, for example, performed under a nitrogen gas or similar inert gas stream. A specific example of the removing operation of materials with a low boiling point is one in which a crude product of the glycerin derivative-modified polysiloxane composition comprising a low boiling point component is placed in a flask having a refluxing cooler, a nitrogen injection port, or the like; and, while supplying nitrogen gas, the internal pressure is reduced and internal temperature is increased and the pressure and temperature are maintained so as to be constant. Thus, the light matter is removed. Here, typically, a pressure reduction parameter is from 0.1 to 10.0 kPa, a heating temperature is from 40 to 120° C., and a treatment time is from 10 minutes to 24 hours.

In the present invention, after the acidizing process, a basic substance may be used to neutralize the glycerin derivative-modified silicone or a composition comprising the same. Examples of the basic substance include sodium hydroxide, potassium hydroxide, calcium hydroxide, barium hydroxide, ammonia water, sodium hydrogen carbonate, and similar inorganic salt groups; amines, pyridines, basic amino acids, and similar organic bases; and the like. An amount of the basic substance is preferably an amount needed to neutralize a reaction system comprising the glycerin derivative-modified polysiloxane composition but, as necessary, the amount of the basic substance may be adjusted to an amount by which weak acidity or weak alkalinity is obtained.

Addition of Alkaline Buffer

In the present invention, after the aforementioned acidizing process, adding an amount corresponding to 100 ppm to 50,000 ppm of an alkaline buffer into the obtained glycerin derivative-modified silicone or a composition comprising the same is preferable. Because of this, a glycerin derivative-modified silicone or a composition comprising the same, that is substantially odor free and causes no odorization over time, can be obtained by more effectively suppressing the odorization over time in a glycerin derivative-modified silicone or composition comprising the same having a reduced odor. A useful alkaline buffer is not particularly limited as long as the alkaline buffer comprises a combination of a strong base and a weak acid. Examples of the alkaline buffer include trisodium phosphate, tripotassium phosphate, trisodium citrate, sodium acetate, and other alkaline buffers. Furthermore, these alkaline buffers can be added to a cosmetic composition raw material and the like comprising a glycerin derivative-modified silicone or a composition that mainly comprises the glycerin derivative-modified silicone, and also can be added to a composition at the preparation stage of or after incorporation in a glycerin derivative-modified silicone composition or cosmetic composition that contains another cosmetic composition raw material and water. The alkaline buffers are useful in more effectively suppressing odorization over time or in the formulation.

The glycerin derivative-modified silicone or composition comprising the same of the present invention can also be subjected to hydrogenation treatment as a process before or after treatment in the presence of an acidic inorganic salt of process [B]. A deodorizing treatment using a hydrogenation reaction may be performed after treatment in the presence of the acidic inorganic salt of the process [B]. On the other hand, the treatment in the presence of the acidic inorganic salt of the process [B] may be performed after deodorizing treatment using a hydrogenation reaction. However, these treatments sometimes lead to increased cost during product production.

<Low Odor Glycerin Derivative-modified Polysiloxane Composition>

It is possible to obtain the low odor glycerin derivative-modified polysiloxane composition of the present invention by the production method of the present invention, which has a process [A], a process [B], and a stripping process that is performed as required. The glycerin derivative-modified organopolysiloxane composition of the present invention generates almost no characteristic odor in hydrophilic silicone over time or in the formulation, and can be suitably applied to fields where it is difficult to provide fragrance free products, including various treatment agents such as those for cosmetic compositions for skin and hair, cleaning agents, fibers, and the like.

Specifically, for the glycerin derivative-modified polysiloxane compositions obtained by the production method of the present invention, odor reduction treatment by hydrolysis in the presence of specific acidic inorganic salts is performed in process [B], thereby eliminating aldehyde odors from these compositions and effectively suppressing odorization in the formulations or over time. Furthermore, in process [B], there is almost no breakage of the silicon-oxygen bonds that form the main chain of polysiloxane and the carbon-oxygen bonds of side chain portions. Thus, structures and properties are stable. As a result, the glycerin derivative-modified polysiloxane composition obtained by the production method of the present invention is suitable for use in cosmetic compositions and external use preparation applications, and the glycerin derivative-modified polysiloxane composition can be suitably incorporated as a raw material for various cosmetic composition and external use preparations. It is particularly preferable to use the glycerin derivative-modified polysiloxane composition at an amount in a range from about 0.1 to 40 wt. % relative to the total weight of a cosmetic composition and external use preparation.

(Carbonyl Value Measurement Method)

Furthermore, the present invention provides a method of accurately and simply quantitating carbonyl compounds, which are believed to be one cause of the odor of a glycerin derivative-modified silicone. The method can quantify the degree of product odor by using a simple and safe means. Thus, it is possible to safely and objectively quantify the degree of odor reduction without performing a sensory test. Also, a product using the glycerin derivative-modified silicone of the present invention or an external use preparation or cosmetic composition comprising the same can explicitly state to consumers that the odor of said product is reduced.

More specifically, the method measures the carbonyl value of the glycerin derivative-modified silicone or a composition comprising the same, based on the absorbance of the reaction solution obtained by reacting a glycerin derivative-modified silicone containing a carbonyl compound or a composition containing the glycerin derivative-modified silicone, and 2,4-dinitrophenylhydrazine (2,4-DNPH) in a reaction medium containing at least one type of monovalent lower alcohol having 1 to 4 carbon atoms. Furthermore, in addition to a compound having a carbonyl group such as an aldehyde or a ketone, the "carbonyl compound" also includes a potential carbonyl compound such as an acetal, propenyl ether, or a similar compound that does not comprise a carbonyl group but generates a carbonyl group by decomposing under certain conditions.

In the present invention, the carbonyl value of a glycerin derivative-modified silicone or a composition comprising the same is determined based on the absorbance of the reaction solution obtained by reacting 2,4-DNPH and a carbonyl compound in the glycerin derivative-modified silicone or the composition comprising the same, and from this carbonyl value, it is possible to measure the total amount of carbonyl (calculated on a propanal basis) in the glycerin derivative-modified silicone or in the composition by using a pre-plotted calibration curve.

The "carbonyl value" is the carbonyl content index value, and is a value obtained by converting the absorbance (absorbance at 430 nm or 460 nm) of the reaction solution, obtained by reacting 2,4-DNPH with the sample, to per 1 g of sample.

Measurement of the carbonyl value uses the property of hydrazone, produced by reacting a carbonyl and 2,4-DNPH in the presence of an acid, that the hydrazone becomes quinoid ions in a base and gives color. The carbonyl value is determined based on the absorbance, which indicates the degree of coloring at 430 nm (a maximum wavelength attributable to saturated carbonyl exists in the vicinity thereof) and at 460 nm (a maximum wavelength attributable to unsaturated carbonyl exists in the vicinity thereof).

The "total amount of carbonyl" is the total amount of carbonyl compound for a glycerin derivative-modified silicone or a composition comprising the same. The concentration of carbonyl compounds (total amount of carbonyl) of various samples (a glycerin derivative-modified silicone or a composition comprising the same) can be measured by obtaining a calibration curve by measuring carbonyl values of standard samples having known concentrations of the carbonyl compound (concentration of propionaldehyde).

In the measurement method of the present invention, at least a monovalent lower alcohol having 1 to 4 carbon atoms is used as the reaction solvent in the reaction between a carbonyl compound and 2,4-DNPH, but it is preferable to use water at the same time.

By using water together with a monovalent lower alcohol having 1 to 4 carbon atoms as the reaction solvent, it is possible to reliably determine the carbonyl value with high precision, even for a sample containing an aldehyde condensation product (potential carbonyl compound) such as an acetal. Thus, it is possible to quantitate the total amount of carbonyls, while taking into consideration carbonyl compounds attributable to these odor-causing substances. Although the reason is unclear, it is inferred that, because water is present in the reaction system, an aldehyde condensation product is decomposed, and the reaction with 2,4-DNPH is reliably performed. In the reaction solvent comprising a monovalent lower alcohol having 1 to 4 carbon atoms and water, the mixing ratio (weight ratio) of the monovalent lower alcohol having 1 to 4 carbon atoms to water is preferably 99.9:0.1 to 50:50, and more preferably 99:1 to 75:25.

In the present invention, "reaction solvent" indicates a solvent that is present in the reaction system containing 2,4-DNPH and a carbonyl compound in a sample. A reaction solvent is formed by using, in addition to (a) a solvent used to prepare a sample solution, (b) a solvent used to prepare the added acid solution, (c) a solvent used to prepare a solution of 2,4-DNPH, and the like.

Each of (a) an alcohol that forms a sample solution, (b) an alcohol that forms an acid solution, and (c) an alcohol that forms a 2,4-DNPH solution need not be a monovalent lower alcohol having 1 to 4 carbon atoms, provided that the alcohol in the reaction solvent resulting from mixture thereof contains a monovalent lower alcohol having 1 to 4 carbon atoms.

In the measurement method of the present invention, it is preferable to use an alcohol as the solvent (hereinafter, "diluent solvent") added to make the volume of a reaction solution to be a prescribed amount when measuring the absorbance of a reaction solution, and it is preferable to use a monovalent lower alcohol having 1 to 4 carbon atoms. Furthermore, all of the diluent solvent need not be an alcohol. Water and/or an organic solvent (organic solvent not having a carbonyl group in its structure, and having low toxicity) can be used as a part of the diluent solvent, within the range that does not impede the effect of the present invention.

The monovalent lower alcohol having 1 to 4 carbon atoms is preferably a saturated alcohol. Examples thereof include methanol, ethanol, n-propanol, i-propanol, n-butanol, i-butanol, and sec-butanol. Among these monovalent lower alcohols, it is preferable to appropriately select the monovalent lower alcohol capable of dissolving or uniformly dispersing the sample, according to the structure and composition of a glycerin derivative-modified silicone or a composition comprising the same. For example, in the case of a glycerin derivative-modified silicone or a composition comprising the same that has a high modification rate attributable to a glycerin derivative and has high hydrophilicity, it is appropriate to select methanol or ethanol. On the other hand, it is often appropriate to select n-propanol or i-propanol, in the case of a glycerin derivative-modified silicone or a composition comprising the same that has a not high hydrophilicity and a low modification rate attributable to a glycerin derivative. Furthermore, it is appropriate to select n-butanol, i-butanol or sec-butanol, in the case of a glycerin derivative-modified silicone or a composition comprising the same, that is comodified by an organic, highly oily group such as a long chain alkyl group. As the monovalent lower alcohol having 1 to 4 carbon atoms, one type can be used independently, or two or more types can be mixed and used.

These alcohols lack toxicity (toxicity such as the toxicity that benzene has), and the alcohols are capable of dissolving various substances having different polarities and molecular weights. Consequently, by using these alcohols as the reaction solvent and diluent solvent, it is possible to safely and easily perform each operation for determining the carbonyl value.

Normally, a monovalent lower alcohol having 1 to 4 carbon atoms having a purity equivalent to the reagent-grade can be used as the monovalent lower alcohol having 1 to 4 carbon atoms without a problem. However, if precise analysis is particularly necessary, it is preferable to use the monovalent lower alcohol having a total content of aldehydes and ketones of at most 3 ppm, preferably at most 2 ppm, and more preferably at most 1 ppm (hereinafter, also called "ultrapure alcohol"). By using an ultrapure alcohol with total content of aldehydes and, ketones of at most 3 ppm as the reaction solvent, it is possible to accurately determine, up to three significant digits, the carbonyl value of a sample with a low carbonyl content (e.g., a carbonyl value of less than 2).

As a method of preparing (refining) an ultrapure alcohol, a method that distills an alcohol under normal pressure or under reduced pressure after adding proper quantities of 2,4-DNPH and an acid lacking oxidative action (e.g., hydrochloric acid or trichloroacetic acid) to the alcohol to be refined and heating and stirring this system over several hours, can be used. Furthermore, it is preferable to perform these refining treatments within 24 hours before measuring the absorbance of the reaction solution.

Additionally, as the ultrapure alcohol, it is preferable to use a commercially available highly pure reagent that has been refined so that a total amount of aldehydes and ketones is 3 ppm or less. Examples of commercially available highly pure reagents that can be used as an ultrapure alcohol include ethanol (99.8%) Infinity Pure; ethanol (99.8%) for precise analysis; ethanol (99.5%) for high-performance liquid chromatography; ethanol (99.5%) for spectrometry; 2-propanol (99.9%) Infinity Pure, 2-propanol (99.9%) for precise analysis; 2-propanol (99.5%) for high-performance liquid chromatography; 2-propanol (99.5%) for spectrometry; 1-propanol (99.8%) Infinity Pure, 1-propanol (99.5%) for high-performance liquid chromatography; methanol (99.8%) Infinity Pure, methanol (99.8%) for precise analysis; methanol (99.5%) for high-performance liquid chromatography; methanol (99.5%) for spectrometry, n-butyl alcohol for high-performance liquid chromatography; n-butyl alcohol for spectrometry (all manufactured by Wako Pure Chemical Industries, Ltd.), and the like.

Furthermore, even for such highly pure reagents, the total amount of aldehydes and ketones increases over time, and sometimes exceeds 3 ppm. In addition, the total amount of aldehydes and ketones exceeds 3 ppm in a relatively short time period after opening (e.g. within 24 hours). Therefore, when particularly precise analysis is required, from the standpoint of satisfying the essential conditions for ultrapure alcohols (i.e. a total amount of aldehydes and ketones is at most 3 ppm), the following highly pure reagents are preferable:

(a) a reagent produced within 6 months before use, and
(b) a reagent opened within 24 hours before use.

In the measurement method of the present invention, the solvent used as the reaction solvent need not be composed solely of a monovalent lower alcohol having 1 to 4 carbon atoms, or a mixed solvent of water and a monovalent lower alcohol having 1 to 4 carbon atoms. A low toxicity organic solvent also may be used as a part of the reaction solvent as long as it does not have a carbonyl group in the structure thereof, within a range that does not impede the effect of the present invention. However, when an organic solvent other than a monovalent lower alcohol having 1 to 4 carbon atoms is used as a part of the reaction solvent, the total amount of aldehydes and ketones contained in the reaction solvent (total excluding water), which is formed by mixing the organic solvent (part) and a monovalent lower alcohol having 1 to 4 carbon atoms (remaining part), is preferably at most 3 ppm.

In the measurement method of the present invention, a basic reaction solution (the reaction solution for absorbance measurement) can be prepared by adding an acid and 2,4-DNPH to a sample solution prepared by dissolving a sample in a solvent, reacting the carbonyl compound in the sample and 2,4-DNPH by heat treating this system, adding an alkali in the system after cooling, and then adjusting the volume of to a prescribed volume with a diluent solvent. Here, it is preferable to use a volumetric flask with a volume of 10 to 100 mL, as the container for preparing a basic reaction solution.

(1) Sample Solution

The solvent used to prepare the sample solution also constitutes the reaction solvent as is, so such a solvent is preferably an ultrapure alcohol or a mixed solvent of an ultrapure alcohol and water. The mass of the sample solution (sample and solvent) used to measure absorbance is normally about 2 to 6 g, and preferably about 5 g. The mass of the sample contained in a sample solution differs according to the carbonyl content of the sample (i.e., the carbonyl value) and the prepared quantity of reaction solution for absorbance measurement (i.e., the volume of the used volumetric flask). However, when, for example, a 50 mL volumetric flask is used to prepare a reaction solution (i.e., the reaction solution for absorbance measurement), the mass of the sample contained in a sample solution is preferably from 5 to 250 mg, and more preferably 10 to 150 mg.

(2) Acids

Examples of acids added to the sample solution include mineral acids such as dilute sulfuric acid, hydrochloric acid, dilute nitric acid, phosphoric acid, and the like; organic acids such as trichloroacetic acid, trifluoroacetic acid, formic acid, acetic acid, sulfonic acid, phenolic acid, and the like; and Lewis acids such as $AlCl_3$, $FeCl_3$, $TiCl_4$, and the like; and the like. These acids can be used alone or in combinations of two or more. Of these, from the standpoint of accurately quantitating the total amount of carbonyl in a highly refined glycerin derivative-modified silicone or a composition comprising the same, trichloroacetic acid, dilute sulfuric acid (particularly the dilute sulfuric acid with a concentration of 20% or less), and hydrochloric acid (particularly the hydrochloric acid with a concentration of 37% or less) are preferable. In addition, the acid used in the present invention is preferably an acid with the highest purity (reagent-grade or higher purity).

These acids may be added as is to a sample solution. However, from the perspective of performing accurate measurement or the like, it is preferable to add the acids in a solution state obtained by dissolving in an appropriate solvent. Furthermore, the solvent used to prepare an acid solution also constitutes the reaction solvent as is, thus, as such the solvent, it is preferable to use a monovalent lower alcohol having 1 to 4 carbon atoms or a mixed solvent of monovalent lower alcohol having 1 to 4 carbon atoms and water. When preparing a reaction solution (a reaction solution that contains from 5 to 250 mg of sample) in a 50 mL volumetric flask, the added amount of acid is preferably from 0.03 to 5.0 g.

(3) 2,4-DNPH

The 2,4-DNPH added to the sample solutions is preferably a 2,4-DNPH having a purity of at least a reagent-grade and containing an equal amount of water. Also, the purity can be further raised by recrystallization or a similar refining operation. 2,4-DNPH can be added as is to a sample solution. However, from the standpoint of performing an accurate measurement, it is preferable to add the 2,4-DNPH in a solution state obtained by dissolving in an appropriate solvent. Furthermore, the solvent used to prepare the 2,4-DNPH solution also constitutes the reaction solvent as is. Thus, as such the solvent, it is preferable to use a monovalent lower alcohol having 1 to 4 carbon atoms, or a mixed solvent of water and a monovalent lower alcohol having 1 to 4 carbon atoms. When preparing a reaction solution (reaction solution that contains from 5 to 250 mg of sample) in a 50 mL volumetric flask, it is preferable to add 0.5 to 100 mg of 2,4-DNPH.

(4) Heat Treatment

A condition for the heat treatment of a mixed solution containing a sample, acid, and 2,4-DNPH is 20 to 180 minutes at 30 to 120° C. (however, the temperature is lower than the boiling point of the reaction solvent). At a treatment temperature below 30° C., it takes a long time to react the 2,4-DNPH and the carbonyl compound in a sample, which is inefficient. On the other hand, when heating at a temperature above 120° C., there is a risk that the generated hydrazone will decompose. When the treatment time is less than 20 minutes, it becomes difficult to complete the reaction with 2,4-DNPH. On the other hand, if the treatment time exceeds 180 minutes, there is a risk that the generated hydrazone will decompose.

(5) Alkali

It is preferable to use an inorganic strong base such as potassium hydroxide, sodium hydroxide, and the like as the alkali added to the reaction solution resulting from the reaction between the 2,4-DNPH and carbonyl compound in a sample. These alkalis can be added as is to a sample solution. However, from the perspective of performing accurate measurement or the like, it is preferable to add these alkalis in a solution state obtained by dissolving in an appropriate solvent. As such solvents, one or two or more solvents can be selected from among solvents that can dissolve an alkali, do not have a carbonyl group in the structure thereof, are compatible with the solvent used as the reaction solvent, and that have low toxicity. Specific examples thereof include monovalent saturated lower alcohols such as methanol, ethanol, 2-propanol, 1-propanol, and the like, or mixed solvents prepared by mixing a proper quantity of water and/or other organic solvent (the organic solvent without a carbonyl group in their structure and having low toxicity) in these solvents. When a reaction solution (reaction solution that contains from 5 to 250 mg of sample) is prepared in a 50 mL volumetric flask, the added amount of alkali is from 0.05 to 5.0 g.

(6) Diluent Solvent

The reaction solution to which alkali was added is adjusted to a specific volume (for example, 50 mL) with a diluent solvent having an alcohol as a main constituent. The alcohol forming the diluent solvent is preferably an ultrapure alcohol.

(7) Specific Preparation Method

An example of a method of preparing a reaction solution for absorbance measurement is as follows. In a 50 mL volumetric flask, 5 g of a sample solution is prepared by dissolving from 5 to 250 mg of a sample in a mixed solvent of water and a monovalent lower alcohol having 1 to 4 carbon atoms. Next, a solution prepared by dissolving from 0.03 to 5.0 g of acid in a monovalent lower alcohol having 1 to 4 carbon atoms and a solution prepared by dissolving from 0.5 to 500 mg of 2,4-DNPH in a monovalent lower alcohol having 1 to 4 carbon atoms are added to the flask. This volumetric flask is then stoppered, and heat treatment is performed for 20 to 180 minutes at 30 to 120° C., thereby reacting the 2,4-DNPH and the carbonyl compound in the sample. After this mixture is cooled to room temperature, a solution prepared by dissolving from 0.05 to 5.0 g of an alkali in an alcohol is added. A diluent solvent composed of an alcohol is then added to adjust the volume of the mixture to 50 mL.

In the measurement method of the present invention, the basic reaction solution obtained as aforementioned is subjected to filtration, as required, after which the absorbance at 430 nm or 460 nm is measured. Here, when the carbonyl compound contained in a sample is estimated to be mainly a saturated carbonyl compound, the absorbance at 430 nm is measured for the reaction solution, and when the carbonyl compound contained in a sample is estimated to be mainly an unsaturated carbonyl compound, the absorbance at 460 nm is measured for the reaction solution. When absorbance is measured, it is preferable that the absorption cell that contains the reaction solution is made of quartz. Also, the length (thickness) of the liquid layer specified by the absorption cell is preferably 1 cm.

It is preferable to measure the absorbance within 10 to 20 minutes after the addition of an alkali to the reaction solution resulting from the reaction of the 2,4-DNPH and the carbonyl compound in a sample. Absorbance measured before 10 minutes after the addition of an alkali sometimes lacks stability. Also, more than 20 minutes after the addition of an alkali, the absorbance tends to drop as a result of the discoloration of the reaction solution. Based on experience with various samples, if the absorbance is measured 15 minutes after the addition of an alkali, the value with best reproducibility is obtained.

In the measurement method of the present invention, the carbonyl value of a sample (a glycerin derivative-modified silicone or a composition comprising the same) is sought based on the absorbance measured as described above. It is possible to measure the total amount of carbonyl in the sample, by using a premeasured calibration curve based on this carbonyl value. Here, the calibration curve is obtained by measuring, according to the method (carbonyl value measurement method), the carbonyl values of a plurality of standard samples whose total amount of carbonyl (propionaldehyde concentration) is known.

For example, a calibration curve is obtained by measuring the carbonyl values of standard samples, for which total amounts of carbonyl (propionaldehyde concentrations) are known, by a method that determines the carbonyl value (CV) by substituting the absorbance ($A_1$) and the absorbance ($A_2$), which are measured by the following processes (1) through (9), into the formula $CV=(A_1-A_2)/B$ (where B is the mass (g) of the sample contained in 5.000 g of sample solution). The same method as aforementioned, which was adopted to obtain this calibration curve, is used to measure the carbonyl value of a sample (a glycerin derivative-modified silicone or a composition comprising the same) for which the total amount of carbonyl is unknown. Based on this carbonyl value and the calibration curve, it is possible to measure the total amount of carbonyl in the sample. Furthermore, if a particularly precise analysis is required, it is preferable that the solvent described below for use in the following processes (1) and (9) contains an ultrapure alcohol and water, and that the solvent described below for use in the following process (7) contains an ultrapure alcohol.

[Processes]
(1) Process that prepares a sample solution by dissolving a sample in a solvent
(2) Process that adds 3 mL of an alcohol solution of 4.3% (wt/vol) trichloroacetic acid to 5.000 g of the sample solution
(3) Process that adds 5 mL of an alcohol solution (0.025% (wt/vol)) of 2,4-DNPH to a mixed solution obtained in the aforementioned process (2)
(4) Process that reacts the carbonyl compound in a sample and 2,4-DNPH by heating the mixed solution obtained in the aforementioned process (3) for 30 minutes at 60° C.
(5) Process that lets stand the reaction solution obtained in the aforementioned process (4) for 30 to 70 minutes at room temperature
(6) Process that adds 10 mL of an alcohol solution (4.0% (wt/vol)) of potassium hydroxide to a reaction solution that was left standing in the aforementioned process (5)
(7) Process that adds a solvent to said reaction solution, prepares a total of 50 mL of reaction solution, and if necessary, performs filtration of the reaction solution, 5 to 10 minutes after the aforementioned process (6)
(8) Process that measures the absorbance ($A_1$) at 430 nm or 460 nm, of the reaction solution obtained in the aforementioned process (7), 10 to 20 minutes after the aforementioned process (6)
(9) Process that, as a blank measurement, measures the absorbance ($A_2$) at 430 nm or 460 nm of a solution obtained by using 5.000 g of solvent instead of using the sample solution and performing the same operations as those in the aforementioned processes (2) through (7)

Furthermore, either the calibration curve measurements (measurements of carbonyl value of standard samples) or the measurements of carbonyl values of unknown samples can be performed before the other measurements.

Next, each process will be described below. Furthermore, the processes (2) through (7) for the preparation of the reaction solution are normally performed using a 50 mL volumetric flask.

Process (1) is a process that prepares a sample solution by dissolving a sample in a solvent containing a monovalent lower alcohol having 1 to 4 carbon atoms. The proportion of sample in a sample solution is modified in accordance with the carbonyl value estimated for the sample. For example, the following settings are preferable: if the carbonyl value is estimated to be less than 6 in the sample, from 2 to 3 wt. % (mass %) (from 100 to 150 mg per 5.000 g of sample solution); if the carbonyl value is estimated to be in a range from 6 to 15 in the sample, from 0.8 to 2 wt. % (mass %) (from 40 to 100 mg per 5.000 g of sample solution); if the carbonyl value is estimated to be in a range from 15 to 30 in the sample, from 0.4 to 0.8 wt. % (mass %) (from 20 to 40 mg per 5.000 g of sample solution); if the carbonyl value is estimated to be in a range from 30 to 60 in the sample, from 0.2 to 0.4 wt. % (mass %) (from 10 to 20 mg per 5.000 g of sample solution); and if the carbonyl value is estimated to be greater than 60 in the sample, less than 0.2 wt. % (mass %) (less than 10 mg per 5.000 g of sample solution).

Additionally, when preparing a sample solution, it is preferable to dilute the sample stepwise. For example, as a method of preparing 5.000 g of 2 wt. % (mass %) sample solution, first, 25.00 g of 8 wt. % (mass %) solution is prepared by dissolving 2.00 g of sample in 23.00 g of a monovalent lower alcohol having 1 to 4 carbon atoms. Next, in a 50 mL volumetric flask, 1.250 g of the 8 wt. % (mass %) solution and a 3.750 g of a monovalent lower alcohol having 1 to 4 carbon atoms is accurately added to dilute the solution four-fold.

In process (2), 3 mL of an alcohol solution of 4.3% (wt/vol) trichloroacetic acid was added to 5.000 g (sample: 0.100 g) of the 2 wt. % (mass %) sample solution obtained in the aforementioned process (1) using a volumetric pipette or the like. The solvent (a monovalent lower alcohol having 1 to 4 carbon atoms) of this alcohol solution is preferably an ultrapure alcohol, when precise analysis is particularly required. In this case, it is preferable to prepare the alcohol solution of trichloroacetic acid by opening a bottle containing 100 mL of ultrapure alcohol, directly adding 4.3 g of trichloroacetic acid to this bottle, covering the bottle, and then shaking the bottle to uniformly mix the contents in the bottle. Also, alcohol solution of trichloroacetic acid is preferably prepared within 24 hours before measuring the absorbance of the reaction solution.

Process (3) is a process that adds 5 mL of an alcohol solution (0.025% (wt/vol)) of 2,4-DNPH to the mixed solution obtained in the aforementioned process (2) using a volumetric pipette or the like. The solvent (a monovalent lower alcohol having 1 to 4 carbon atoms) of this alcohol solution of 2,4-DNPH is preferably an ultrapure alcohol, when particularly precise analysis is required. In this case, the alcohol solution of 2,4-DNPH is preferably prepared by opening a bottle containing 100 mL of ultrapure alcohol, directly adding 50 mg of 2,4-DNPH (reagent-grade product containing an equal amount of water) to this bottle, covering the bottle, and then putting the bottle into an ultrasonic bath for about 5 minutes to completely dissolve the 2,4-DNPH in the bottle. In addition, the alcohol solution of 2,4-DNPH is preferably prepared within 24 hours before measuring the absorbance of the reaction solution. It is preferable to add more water to hydrolyze the precursors of the carbonyl compound of acetal and the like present in the sample, to detect the precursors as carbonyl compounds.

In process (4), the mixed solution obtained in the aforementioned process (3) is heated for 30 minutes at 60° C. to react the 2,4-DNPH and the carbonyls in the sample, thereby yielding a reaction solution containing hydrazone.

In process (5), the reaction solution obtained in the process (4) is cooled by letting the reaction solution stand for 30 to 70 minutes at room temperature.

In process (6), 10 mL of alcohol solution of potassium hydroxide (4.0% (wt/vol)) was added and mixed to the reaction solution after letting it stand, using a volumetric pipette or the like. As a result, the reaction solution exhibits basicity, and the generated hydrazone becomes quinoid ions and gives color. The solvent (a monovalent lower alcohol having 1 to 4 carbon atoms) of this alcohol solution of potassium hydroxide is preferably an ultrapure alcohol, when particularly precise analysis is required. In this case, the alcohol solution of potassium hydroxide is preferably prepared by opening a bottle containing 100 mL of ultrapure alcohol, directly adding 4.0 g of potassium hydroxide (pellet shaped reagent-grade product) to this bottle, and covering the bottle, and after shaking until the pellets disappear, this bottle is placed in an ultrasonic bath for about 5 to 10 minutes, to completely dissolve the potassium hydroxide in the bottle. Also, it is preferable to prepare the alcohol solution of potassium hydroxide within 24 hours before measuring the absorbance of the reaction solution.

In process (7), 5 to 10 minutes after the aforementioned process (6), a diluent solvent composed of a monovalent lower alcohol having 1 to 4 carbon atoms (preferably an ultrapure alcohol) is added to the reaction solution, to prepare a total amount of 50 mL of reaction solution (basic reaction solution). If this reaction solution is nonuniform as a result of the precipitation of neutralized salt, it is possible to obtain a uniform solution by performing additional filtration.

In process (8), for the reaction solution obtained in the aforementioned process (7), the absorbance ($A_1$) is measured at 430 nm (when the carbonyl in the sample is estimated to be mainly a saturated carbonyl) or at 460 nm (when the carbonyl in the sample is estimated to be mainly an unsaturated carbonyl).)The absorbance must be measured 10 to 20 minutes after addition of the alcohol solution of potassium hydroxide of the aforementioned process (6), and it is most preferable to measure absorbance 15 minutes after the addition of the alcohol solution of potassium hydroxide.

In process (9), for blank measurement, 5.000 g of a monovalent lower alcohol having 1 to 4 carbon atoms are used instead of the aforementioned sample solution, and for the solution obtained by performing the same operations as in the aforementioned processes (2) through (7) (i.e., addition of alcohol solution of trichloroacetic acid; addition of alcohol solution of 2,4-DNPH and addition of water; heating and cooling of the obtained mixed solution; addition of alcohol solution of potassium hydroxide; and addition of diluent solvent composed of a monovalent lower alcohol having 1 to 4 carbon atoms), the absorbance ($A_2$) at 430 nm or 460 nm is measured.

It is possible to determine the carbonyl value (CV) by substituting the absorbance ($A_1$) obtained by the aforementioned processes (1) through (8) and the absorbance ($A_2$) obtained by the aforementioned process (9), respectively, into the formula: $CV=(A_1-A_2)/B$.))In the above formula, B is the weight (mass) (g) of the sample contained in 5.000 g of sample solution, and in a 2 wt. % (mass %) sample solution, B is 0.1 (5.000×0.02).

The glycerin derivative-modified silicone or composition comprising the same obtained by the production method of the present invention, has a low odor, and the carbonyl value measured by the method is reduced to 3.0 Abs/g or less. On the other hand, even after incorporation in a cosmetic composition or the like, the glycerin derivative-modified silicone with a reduced carbonyl value has almost no perceptible odor, and agrees well with the results of the sensory test. Furthermore, for the low odor glycerin derivative-modified silicone or composition comprising the same obtained by the production method of the present invention, the carbonyl value measured by the aforementioned method is more preferably 2.0 Abs/g or less, and still more preferably 1.0 Abs/g or less. Furthermore, when acidizing is not performed, the carbonyl value of a glycerin derivative-modified silicone or a composition comprising the same is generally not less than 9.0 Abs/g, and a distinct odor is detected.

Unlike the conventional low odor polyether-modified silicone, the low odor glycerin derivative-modified silicone of the present invention is hardly susceptible to deterioration due to oxidation by oxygen in the air. Thus, it is not necessary to add a phenol, a hydroquinone, a benzoquinone, an aromatic amine, a vitamin, or similar antioxidant in order to prevent oxidation deterioration; or take steps to increase oxidation stability. However, adding such an antioxidant, for example, BHT(2,6-di-t-butyl-p-cresol), vitamin E, or the like, will result in a further increase in stability. In this case, an added amount of the antioxidant that is used is in a range (by weight (mass)) from 10 to 1,000 ppm, and preferably from 50 to 500 ppm, of the glycerin derivative-modified silicone.

Raw material for use in an external use preparation or a cosmetic composition The low odor glycerin derivative-modified silicone or the composition comprising the same obtained by using the production method of the present invention, has little odor, and odorization in the formulation or over time are suppressed. Moreover, there is the advantage of breaking almost no silicon-oxygen bonds forming the main chain of the glycerin derivative-modified silicone or carbon-oxygen bonds forming the side chains. Therefore, the low odor glycerin derivative-modified silicone of the present invention can be preferably applied as raw material for an external use preparation and a cosmetic composition used on the human body.

A proportion of the low odor glycerin derivative-modified silicone in the raw material for an external use preparation and a cosmetic composition is preferably from 10 to 100 wt. % (mass %), more preferably from 20 to 100 wt. % (mass %), and even more preferably from 30 to 100 wt. % (mass %), relative to the total weight (mass) of the raw material. This is because the low odor glycerin derivative-modified silicone according to the present invention can be used as a raw material of an external use preparation or cosmetic composition by diluting the low odor glycerin derivative-modified silicone in a suitable solvent, such as a silicone oil, an organic oil, and an alcohol. A proportion of the raw material compounded in the external use preparation or the cosmetic composition is not particularly limited but, for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) based on the total weight (mass) of the external use preparation or the cosmetic composition.

Furthermore, the glycerin derivative-modified silicone or the composition comprising the same of the production method according to the present invention can be used in the same intended uses as those of the co-modified organopolysiloxanes described in the aforementioned Patent Document 20 (WO2011/049247) or Patent Document 21 (WO2011/049248), according to the structure and the type of functional group other than the glycerin derivative-modified group. The glycerin derivative-modified silicone or the composition comprising the same is suitable for use as a thickening agent or gelling agent for an oily raw material, a surfactant (emulsifier), or a variety of treatment agents (powder dispersing agent or surface treatment agent), particularly for use as a powder treatment agent, for use as a cosmetic composition raw material, and the like. The glycerin derivative-modified silicone or the composition comprising the same obtained by the production method of the present invention can be combined with an arbitrary cosmetic raw material component, can be used in the same way as the co-modified organopolysiloxanes disclosed in Patent Document 20 and Patent Document 21, in external use preparations, and especially in formulations, types, and formulation examples of cosmetic compounds, and can be blended in a variety of cosmetic compositions. Furthermore, the glycerin derivative-modified silicone obtained via the production method according to the present invention, or the composition comprising the same can be used as a tactile sensation improver, a moisturizing agent, a binder, a surface treatment agent, a skin adhesive, a film-forming agent, a viscosity adjusting agent and a thickening agent.

External Use Preparation and Cosmetic Composition

The low odor glycerin derivative-modified silicone of the present invention or the raw materials for an external use preparation or a cosmetic composition composed of the low odor glycerin derivative-modified silicone of the present invention can be suitably incorporated into an external use preparation or a cosmetic composition, and can form the external use preparations and the cosmetic compositions of the present invention. These exhibit the merits of low odor, particularly in anti-perspirant compositions, whose active component is an acidic substance, weakly acidic external use preparations or cleaning agents, which are expected to exhibit a peeling effect, cosmetic compositions, or the like (these formulations are acidic, so they are considered to readily generate unusual odors attributable to modified silicone).

The external use preparation according to the present invention is not particularly limited, provided that it is a composition for application to the human body as a cosmetic composition or a medicament. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The external use preparation is a product to be applied to human skin, nails, hair, and the like and, for example, medicament active components can be compounded therein and used in the treatment of various disorders. The cosmetic composition is also a product to be applied to human skin, nails, hair, and the like, and is used for beauty purposes. The external use preparation or cosmetic composition is preferably an anti-perspirant, a skin cleansing agent, a skin conditioner, a skin cosmetic composition product, a hair cleansing agent, an external use preparation for hair or a hair cosmetic composition.

The anti-perspirant, skin cleansing agent, skin external use preparation, or skin cosmetic composition of the present invention contains the low odor glycerin derivative-modified silicone of the present invention, and the form thereof is not particularly limited, but may be in the form of a solution, milk-like, cream-like, solid, semi-solid, paste-like, gel-like, powder-like, multi-layer, mousse-like, or a water-in-oil or oil-in-water emulsion composition. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

Similarly, the hair cleansing agent, hair external use preparation or the hair cosmetic composition product according to the present invention contains the low odor glycerin derivative-modified silicone of the present invention and can be used in various forms. For example, the hair cleansing agent, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair cleansing agent, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. These various forms can be used as shampooing agents, rinsing agents, conditioning agents, setting lotions, hair sprays, permanent wave agents, mousses, hair colorants, and the like.

In addition, the type, form and container of the cosmetic composition or external use preparation composition according to the present invention are the same as those disclosed by the applicants in paragraphs [0230] to [0233] and so on of the above-mentioned patent document 21 (WO 2011/049248).

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

[(F) Powder or Coloring Agent]

A powder or coloring agent (F), which is used in the cosmetic composition or external use preparation according to the present invention, is one that is commonly used as a component of a cosmetic composition, and includes white or colored pigments and extender pigments. The white and colored pigments are used to impart color and the like to the cosmetic composition, and the extender pigments are used to improve the feeling to touch and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range from 1 nm to 100 μm. When compounding the powder and/or coloring agent as a pigment, preferably one or two or more selected from an inorganic pigment powder, an organic pigment powder, and a resin powder having an average diameter in a range from 1 nm to 20 μm is compounded.

Examples of the powder include inorganic powders, organic powders, surfactant metal salt powders (metallic soaps), colored pigments, pearl pigments, metal powder pigments, and the like. In addition, compound products of the powders can also be used. Furthermore, it is possible to subject the surface of these to water-repellent treatment.

These specific examples are the same as the powders and coloring agents disclosed by the applicants in paragraphs [0150] to [0152] of the above-mentioned patent document 21 (WO 2011/049248).

Of the exemplified powders, a particular explanation will be given of a silicone elastomer powder. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group and the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by carrying out surface treatment using the co-modified organopolysiloxane, it is possible to impart a moist feeling to touch without reducing the suede-like feeling to touch of a silicone elastomer powder. Furthermore, when blending the co-modified organopolysiloxane in addition to a silicone elastomer powder in a cosmetic composition, it is possible to improve the dispersion stability of the powder in the overall cosmetic composition and obtain a cosmetic composition that is stable over time.

The silicone elastomer powder can be in various forms such as spherical, flat, amorphous, and the like. The silicone elastomer powder may be in the form of an oil dispersion. With the cosmetic composition of the present invention, a silicone elastomer powder having a particle shape, having a primary particle size in a range of 0.1 to 50 μm observed using an electron microscope and/or the average primary particle size in a range of 0.1 to 50 μm measured by laser diffraction/scattering method, and having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those disclosed by the applicants in paragraph [0168] of the above-mentioned patent document 21 (WO 2011/049248), and may be a silicone elastomer powder that has been subjected to a variety of water-repellent treatments, as disclosed in paragraphs [0150] to [0152].

(G) Oil Agent

The oil agent used in the cosmetic composition or external use preparation according to the present invention is preferably one or more oil agents selected from among silicone oils, non-polar organic compounds, and lowly polar organic compounds that are liquid at 5 to 100° C. (G), and the non-polar organic compound and lowly polar organic compound is preferably a hydrocarbon oil, or fatty acid ester oil. These are components that are particularly widely used as base materials for make-up cosmetic compositions, but it is possible to additionally use one or more type of compound selected from among publicly known vegetable oils and fats, animal oils and fats, higher alcohols, liquid fatty acid triglycerides, artificial sebum, and fluorine-based oils as well as these oil agents. The above low odor glycerin derivative-modified silicone exhibits superior dispersibility also for non silicone oil agents of these. Therefore, hydrocarbon oil and fatty acid ester oil can be stably incorporated into a cosmetic composition, and the moisture retaining property of these non silicone based oil agents can be retained. Therefore, the aforementioned low odor glycerin derivative-modified silicone can improve the stability over time in a cosmetic composition of these non silicone based oil agents.

In addition, by using a hydrocarbon oil and/or fatty acid ester oil in combination with a silicone oil, it is possible to retain moisture in the skin in addition to the refreshing feeling to touch inherent in silicone oils and impart a cosmetic composition with a moisturizing feel (also known as a "luxurious feeling to touch") that moisturizes skin and hair and a smooth feeling to touch, and this also has the advantage of not impairing the stability over time of a cosmetic composition. Furthermore, with a cosmetic composition comprising the hydrocarbon oil and/or fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone based oil agent (e.g. a hydrocarbon oil, a fatty acid ester oil, or the like), the cosmetic composition comprising a non silicone based oil agent along with a silicone oil is advantageous in that a smoother, more luxurious feeling to touch is imparted.

These oil agents are the same as those disclosed by the applicants in paragraphs [0130] to [0135] and [0206] and so on in the above-mentioned patent document 21 (WO 2011/049248). Examples of the fluorine-based oil include perfluoropolyether, perfluorodecalin, perfluorooctane, and the like.

It is possible to further blend water (H) in the cosmetic composition or external use preparation of the present invention, and the cosmetic composition or external use preparation of the present invention may be in the form of an oil-in-water type emulsion or a water-in-oil type emulsion. In this case, the cosmetic composition of the present invention or the external use preparation displays superior emulsion stability and sensation during use. The preparation of a hydrous cosmetic composition or emulsion cosmetic composition is the same as that disclosed by the applicants in paragraphs [0128] to [0146] in the above-mentioned patent document 21 (WO 2011/049248).

It is possible to further blend another surfactant (I) in the cosmetic composition or external use preparation of the present invention. These surfactants are cleansing components for skin or hair or components that function as emulsifiers for oil agents, and can be selected as appropriate according to the type and function of the cosmetic composition. More specifically, other surfactants can be selected from among the group comprising anionic surfactants, cationic surfactants, non-ionic surfactants, amphoteric surfactants and semipolar surfactants, but use in combination with a silicone-based non-ionic surfactant is particularly preferred.

These surfactants are the same as those disclosed by the applicants in paragraphs [0162], [0163] and [0195] to [0201] and so on in the above-mentioned Patent Document 21 (WO 2011/049248). The low odor glycerin derivative-modified silicone used in the present invention has a hydrophilic moiety and a hydrophobic moiety in the molecule, and therefore functions as a dispersing agent. Therefore, when combined with a silicone-based non-ionic surfactant, the low odor glycerin derivative-modified silicone functions as an aid to enhance the stability of the non-ionic surfactant, and may improve the overall stability of the formulation. In particular, the low odor glycerin derivative-modified silicone can be advantageously used in combination with a polyoxyalkylene-modified silicone, a polyglyceryl-modified silicone, a glyceryl-modified silicone, a sugar-modified silicone, and a sugar alcohol-modified silicone. Moreover, as necessary, a silicone-based nonionic surfactant in which an alkyl branch, a straight chain silicone branch, a siloxane dendrimer branch, or the like is provided along with the hydrophilic group can be advantageously used.

Depending on the intended use thereof, the cosmetic composition or external use preparation of the present invention can contain one or two or more polyhydric alcohols and/or lower monohydric alcohols as a component (J). These alcohols are the same as those disclosed by the applicants in paragraphs [0159] and [0160] and so on in the above-mentioned Patent Document 21 (WO 2011/049248).

Depending on the purpose thereof, the cosmetic composition or the external use preparation of the present invention can include one or two or more inorganic salts and/or organic salts as a component (K). These salts are the same as those disclosed by the applicants in paragraph [0161] and so on in the above-mentioned Patent Document 21 (WO 2011/049248).

Depending on the purpose thereof, the cosmetic composition or the external use preparation of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (N). These silicone components are the same as those disclosed by the applicants in paragraphs [0161] to [0193] and so on in the above-mentioned patent document 21 (WO 2011/049248).

Depending on the intended use thereof, the cosmetic composition or external use preparation of the present invention can contain one or two or more water-soluble polymers as a component (P). These water-soluble polymers are the same as those disclosed by the applicants in paragraphs [0201] and so on in the above-mentioned patent document 21 (WO 2011/049248).

Depending on the intended use thereof, the cosmetic composition or external use preparation of the present invention can contain one or two or more ultraviolet light blocking component as a component (S). These ultraviolet light blocking components are the same as the organic and inorganic ultraviolet light blocking components disclosed by the applicants in paragraphs [0202] to [0204] and so on in the above-mentioned Patent Document 21 (WO 2011/049248). The ultraviolet light blocking components that can be used particularly preferably include at least one type selected from among the group comprising fine particulate titanium oxide, fine particulate zinc oxide, paramethoxy cinnamic acid 2-ethylhexyl, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris [4-(2-ethylhexyloxycarbonyl)anilino]1,3,5-triazine {INCI: octyl triazone}, 2,4-bis{[4-(2-ethyl-hexyloxy)-2-hydroxy]phenyl}-6-(4-methoxyphenyl)-1,3,5-triazine {INCI: bis-ethylhexyloxyphenol methoxyphenyltriazine (product name: Tinosorb S™)}. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with a raw material for a cosmetic composition that contains the aforementioned low odor glycerin derivative-modified silicone in the cosmetic composition or the external use preparation of the present invention, it is possible to stably disperse the ultraviolet light blocking component in the cosmetic composition while improving the feeling to touch and storage stability of the overall cosmetic composition, and it is therefore possible to impart the cosmetic composition with excellent ultraviolet light blocking properties.

Various components other than the components described above can be used in the cosmetic composition or external use preparation of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These optional cosmetic product components are the same as those disclosed by the applicants in paragraphs [0207], [0208] and [0220] to [0228] and so on in the above-mentioned patent document 21 (WO 2011/049248).

Additionally, in cases where the external use preparation or the cosmetic composition according to the present invention is an anti-perspirant, or depending on the purpose thereof, the external use preparation or the cosmetic composition can contain an anti-perspiration active component and/or a deodorant agent. These anti-perspiration components and deodorant components are the same as those disclosed by the applicants in paragraphs [0209] to [0219] and so on in the above-mentioned patent document 21 (WO 2011/049248). Similarly, in cases where the external use preparation or the cosmetic composition according to the present invention is an anti-perspirant composition, the preparation and method of use of the various anti-perspirant compositions are the same as those disclosed by the applicants in paragraphs [0234] to [0275] and so on of the above-mentioned patent document 21 (WO 2011/049248).

INDUSTRIAL APPLICABILITY

The method of producing the low odor glycerin derivative-modified silicone or a composition comprising the same of the present invention can be implemented inexpensively and simply. The low odor glycerin derivative-modified silicone or a composition comprising the same produced by the method has a reduced odor, and can be preferably used as a raw material for an external use preparation or a cosmetic composition, and it is possible to provide an external use preparation, medicament, and cosmetic composition that is odor free or lacks an unpleasant odor.

In addition, the carbonyl value measurement method of the present invention is capable of accurately and simply quantitating a carbonyl compound. Therefore, the method can be preferably used for the evaluation of the odor of a product of an external use preparation, cosmetic raw material, external use preparation, or cosmetic composition that contains a low odor glycerin derivative-modified silicone obtained by the production method of the present invention.

EXAMPLES

Hereinafter, the present invention is described in detail with reference to Practical Examples and Comparative Examples, but it should be understood that the present invention is not limited to these Practical Examples. Also, the compositions that contain the glycerin derivative-modified silicone of Comparative Examples 2 and 3 and Practical Example 2 is "gummy" and has an extremely high viscosity. Thus, it is difficult to reduce the odor of these glycerin derivative-modified silicones by a hydrogenation treatment such as that in Comparative Example 4.

In the compositional formulae below, Me denotes a methyl ($—CH_3$) group, a $Me_3SiO$ group (or a $Me_3Si$ group) is represented by "M", a $Me_2SiO$ group is represented by "D", a MeHSiO group is represented by "DH", and units in which methyl groups in M and D are modified by a substituent group are represented by "$M^R$" and "$D^R$". Additionally, in the production examples, "IPA" represents isopropyl alcohol.

Comparative Example 1

<Synthesis of Comparative Silicone Compound RE-1>

177.5 g of a methylhydrogenpolysiloxane expressed by the average composition formula $MD_{72}D^H{}_{12}M$, 107.6 g of a vinyl tris(trimethylsiloxy)silane expressed by the average composition formula $CH_2$=$CH$—$Si(OSiMe_3)_3$, 14.7 g of a glycerinmonoallyl ether represented by the structural formula $CH_2$=$CH$—$CH_2$—$OCH_2CH(OH)CH_2OH$, and 90 g of IPA were placed in a reaction vessel, and heated to 40° C. while agitating under a nitrogen stream. 0.130 g of an IPA solution of a platinum-1,3-divinyl-1,1,3,3-tetramethyldisiloxane complex (Pt concentration=4.5 wt. %) was added thereto, and the mixture was reacted for three hours at 80° C. Then, 2 g of the reaction liquid was sampled, and it was confirmed that the reaction was complete through an alkali decomposition gas generation method. The reaction liquid was heated under reduced pressure so as to distill off low-boiling components. Thus, 289 g of a substantially colorless, semi-transparent uniform liquid composition comprising a glycerin derivative-modified silicone having a siloxane dendron structure expressed by the average composition formula: $MD_{72}D^{R*31}{}_9D^{R*21}{}_3M$ was obtained.

In this formula, $R^{*21}$ and $R^{*31}$ are as described below.

$R^{*21}$=—$C_3H_6OCH_2CH(OH)CH_2OH$

$R^{*31}$=—$C_2H_4Si(OSiMe_3)_3$

Furthermore, in this composition, the generation of the strong aldehyde odor was detected 1 month after production.

Comparative Example 2

<Synthesis of Comparative Silicone Compound RE-2>

Step 1: 110.3 g of a methylhydrogenpolysiloxane expressed by the average composition formula $MD_{330}D^H{}_{80}M$, and 12.1 g of a vinyl tris(trimethylsiloxy)silane expressed by the average composition formula $CH_2$=$CH$—$Si(OSiMe_3)_3$ were placed in a reaction vessel. Then, 0.25 g of an IPA solution of a platinum-1,3-divinyl-1,1,3,3-tetramethyldisiloxane complex (Pt concentration: 0.4 wt. %) was added at 35° C. while agitating under a nitrogen stream. After the temperature rise caused by generated heat leveled off, 12.1 g of the vinyl tris(trimethylsiloxy)silane (second addition) was added and the mixture was reacted in the same way. After the temperature rise caused by generated heat leveled off, 12.1 g of the vinyl tris(trimethylsiloxy)silane (third adding) was added and the mixture was reacted in the same way. Then, 2 g of the reaction liquid was sampled and it was confirmed that the reaction rate was not in error through an alkali decomposition gas generation method.

Step 2: 8.0 g of a polyglycerin monoallyl ether, 0.02 g of natural vitamin E, and 60 g of IPA were added to the reaction liquid. Then, 0.25 g of the platinum catalyst solution described above was added. After the temperature rise caused by generated heat leveled off, the mixture was reacted for two hours at from 65 to 80° C. and, thereafter, it was confirmed that the reaction rate was not in error through the same method described above.

Step 3: 15.1 g of hexadecene (α olefin purity=91.7%) was added to a reaction solution at about 65° C. After the temperature rise caused by generated heat leveled off, 15.1 g of the hexadecene (second addition) was added and the mixture was reacted in the same way. After the temperature rise caused by generated heat leveled off, 15.2 g of the hexadecene (third adding) and 0.25 g of the platinum catalyst solution were added, and the mixture was reacted for three hours at from 65 to 80° C. 2 g of the reaction liquid was sampled and it was confirmed that the reaction was complete through an alkali decomposition gas generation method.

Step 4: 200 g of a caprylyl methicone diluent (SS-3408) was added and dissolved and, thereafter, the mixture was heated under reduced pressure to remove IPA and low-boiling components by distillation. Moreover, filtration was performed at 70° C., and 380 g of a 50:50 (weight ratio) mixture of caprylyl methicone and a composition containing a glycerin derivative-modified silicone having both a long chain alkyl group and a siloxane dendron structure expressed by the average composition formula $MD_{330}D^{R^{*12}}{}_{45}D^{R^{*31}}{}_{30}D^{R^{*22}}{}_{5}M$ was obtained. This mixture was milky white and uniformly gummy at room temperature.

In this formula, $R^{*12}=-C_{16}H_{33}$.

$R^{*31}=-C_2H_4Si(OSiMe_3)_3$ $R^{*22}$ is expressed by $-C_3H_6O-X$, where "X" is the tetraglycerin portion.

In this mixture, the generation of the aldehyde odor was detected 1 month after production. Moreover, the polyglycerin monoallyl ether was synthesized by ring-opening polymerizing 3 mole equivalents of glycidol with 1 mole of a glycerin monoallyl ether, and had a structure in which an average of 4 moles of glycerin were added. Moreover, the glycerin monoallyl ether has two hydroxyl groups that can both react with the glycidol and the polyglycerin portion therefore includes not only a straight chain structure, but also a branched structure.

Comparative Example 3

<Synthesis of Comparative Silicone Compound RE-3>

150 g of a 50:50 (weight ratio) mixed solution of caprylyl methicone and the glycerin derivative-modified silicone obtained in Comparative Example 2 expressed by the average composition formula: $MD_{330}D^{R^{*12}}{}_{45}D^{R^{*31}}{}_{30}D^{R^{*22}}{}_{5}M$, 45 g of IPA, and 1.1 g of 0.1% phosphoric acid water were fed into a reaction vessel. While this mixture was stirred under a nitrogen stream, acidizing was performed for 1.5 hours at 75 to 80° C. Then IPA and low-boiling components were removed under reduced pressure at 70° C., and when distillation was stopped, the pressure was restored (first acidizing). Next, 45 g of IPA and 1.1 g of water were added and 1 hour of treatment was similarly performed. Then, after IPA and low-boiling components were removed, the pressure was restored (second acidizing). Further, 45 g of IPA and 1.1 g of water were added, and treatment was similarly performed for 1 hour (third acidizing). Then, neutralization was performed by blowing ammonia gas for 12 minutes at a flow rate of 4 mL/min. IPA and low-boiling components were removed by heating at 75 to 85° C. under reduced pressure, thereby yielding 147 g of a 50:50 (weight ratio) mixture of caprylyl methicone and a composition containing glycerin derivative-modified silicone having a long chain alkyl group and a siloxane dendron structure expressed by the average composition formula $MD_{330}D^{R^{*12}}{}_{45}D^{R^{*31}}{}_{30}D^{R^{*22}}{}_{5}M$.

In this formula, $R^{*12}$, $R^{*31}$, and $R^{*22}$ are the same as described above.

This mixture was milky white and uniformly gummy at room temperature, and a slight aldehyde odor was detected 1 month after production.

Comparative Example 4

<Synthesis of Comparative Silicone Compound RE-4>

111.6 g of a methylhydrogenpolysiloxane expressed by the average composition formula $MD_{61}D^H{}_{15}M$ was placed in a reaction vessel. Then a mixture comprising 30.9 g of a single-terminal vinyl-modified dimethylpolysiloxane represented by the structural formula $CH_2=CHSiMe_2(OSiMe_2)_6OSiMe_3$ and 0.10 g of a toluene solution of a platinum-1,3-divinyl-1,1,3,3-tetramethyldisiloxane complex (Pt concentration: 0.5 wt. %) was added dropwise, and the mixture was agitated at room temperature, thereby obtaining a linear siloxane branched-type polysiloxane intermediate.

In addition, 7.0 g of triglycerin monoallyl ether, 50.4 g of 1-dodecene (α olefin purity=95.4%), 100 g of IPA, and 0.40 g of an IPA solution of platinum-1,3-divinyl-1,1,3,3-tetramethyldisiloxane complex (Pt concentration: 0.5 wt. %) were fed into another reaction vessel, and previously synthesized linear siloxane branched-type polysiloxane was added dropwise under solvent reflux, while stirring under a nitrogen stream. After the adding was completed, heating and agitating was continued for 3 hours. Then, 2 g of the reaction liquid was sampled and it was confirmed that the reaction was complete through an alkali decomposition gas generation method.

Next, the reaction liquid was moved to an autoclave and 4.0 g of a sponge nickel catalyst, 2.0 g of water, and 2.0 g of IPA was added. Then, hydrogen gas was introduced and hydrogenation treatment was carried out for 6 hours under the following conditions: 110° C., 0.9 MPa. The reaction mixture was cooled to 60° C. after the treatment and blown with hydrogen gas. Then, purging with nitrogen gas was performed three times. Next, the sponge nickel catalyst was removed via precision filtration. Thus, 204 g of a colorless, transparent filtrate was obtained.

This filtrate was placed in a separate reaction vessel and maintained for one hour at 100° C. and 20 Torr under a nitrogen stream so as to distill off low-boiling components. Thus, 138 g of a deodorized, substantially colorless, semi-transparent and uniform liquid composition comprising a glycerin derivative-modified silicone expressed by the average composition formula: $MD_{61}D^{R^{*11}}{}_{12}D^{R^{*13}}{}_{2}D^{R^{*23}}{}_{1}M$ was obtained.

In this formula, $R^{*11}=-C_{12}H_{25}$.

$R^{*13}=-C_2H_4SiMe_2(OSiMe_2)_6OSiMe_3$ $R^{*23}=-C_3H_6O-X$, where X is the triglycerin moiety.

Even 1 month after this composition was produced, generation of the aldehyde odor was not detected.

Practical Example 1

<Synthesis of Low Odor Glycerin Derivative-modified Silicone No. 1>

An aqueous solution prepared by dissolving 0.15 g of sodium hydrogensulfate monohydrate, and 150 g of a composition containing the glycerin derivative-modified silicone obtained in Comparative Example 1 expressed by the average composition formula $MD_{72}D^{R*31}{}_9D^{R*21}{}_3M$ were fed into a reaction vessel. After this mixture was acidized for 1.5 hour at 70 to 80° C. while stirring under a nitrogen stream, the low-boiling components were removed at 70° C. under reduced pressure, and the pressure was restored when water droplets disappeared from the system (first acidizing). Next, 15 g of purified water was added and treatment was carried out in the same way for 1 hour, low-boiling components were distilled off, and the pressure was restored when water droplets in the system had disappeared (second acidizing). The same operations were repeated (third acidizing), thereby yielding 146 g of a milky white, uniform liquid composition containing a low odor glycerin derivative-modified silicone having the siloxane dendron structure expressed by the average composition formula $MD_{72}D^{R*31}{}_9D^{R*21}{}_3M$.

In this formula, $R^{*21}$ and $R^{*31}$ are the same as described above.

Even 1 month after this composition was produced, generation of the aldehyde odor was not detected.

Practical Example 2

<Synthesis of Low Odor Glycerin Derivative-modified Silicone No. 2>

200 g of a 50:50 (weight ratio) mixed solution of caprylyl methicone and a composition containing the glycerin derivative-modified silicone obtained in Comparative Example 2 expressed by the average composition formula $MD_{330}D^{R*12}{}_{45}D^{R*31}{}_{30}D^{R*22}{}_5M$, 60 g of IPA, and an aqueous solution prepared by dissolving 0.21 g of sodium hydrogensulfate monohydrate in 20 g of purified water were fed into a reaction vessel. Then, acidizing was performed for 1 hour at 70 to 80° C. while stirring under a nitrogen stream. After distilling off IPA and low-boiling components at 70° C. under reduced pressure, the pressure was restored when water droplets in the system had disappeared (first acidizing). Next, after 60 g of IPA and 20 g of water were added and treatment was carried out in the same way for 1 hour, IPA and low-boiling components were distilled off, and the pressure was restored when water droplets in the system had disappeared (second acidizing). The same operations were repeated (third acidizing), thereby yielding 194 g of a 50:50 (weight ratio) mixed solution of caprylyl methicone and a composition containing a low odor glycerin derivative-modified silicone having a long chain alkyl group and a siloxane dendron structure expressed by the average composition formula $MD_{330}D^{R*12}{}_{45}D^{R*31}{}_{30}D^{R*22}{}_5M$. In this formula, $R^{*12}$, $R^{*31}$, and $R^{*22}$ are the same as described above.

This mixture was milky white and uniformly gummy at room temperature, and the generation of aldehyde odor was not detected even 1 month after production.

[Measurement of Total Amount of Carbonyl]

In accordance with the following procedure, the total amounts of carbonyl in the modified silicone compositions (samples) obtained in Practical Examples 1 and 2 and Comparative Examples 1 to 4 were measured as the "carbonyl value (COV)," to quantify the carbonyls responsible for the odors in the compositions.

Preparation Example 1A

Reagent-grade n-butanol (A) was weighed out into a 100 mL brown glass bottle, and 4.3 g of reagent-grade trichloroacetic acid was added. The bottle was covered and then shaken to homogenize it, thereby preparing an alcohol solution of trichloroacetic acid (acid concentration: 4.3% (wt/vol)). Hereinafter, this solution is called "trichloroacetic acid solution (1A)."Furthermore, this preparation operation was performed within 3 hours before measurement of absorbance.

Preparation Example 2A

Reagent-grade n-butanol (A) was weighed out into a 100 mL brown glass bottle. Then 50 mg of 2,4-dinitrophenylhydrazine (reagent-grade product containing equal amount of water; abbreviated hereinafter as "2,4-DNPH") was added. After the bottle was covered, the bottle was subjected to an ultrasonic bath for 10 minutes. Thereby the 2,4-DNPH was completely dissolved by alcohol (A), and a 0.025% (wt/vol) 2,4-DNPH alcohol solution was prepared. Hereinafter, this solution is called "2,4-DNPH solution (2A)."Furthermore, this preparation operation was performed within 3 hours before measurement of absorbance.

Preparation Example 3B

Reagent-grade ethanol (B) was weighed out into a 100 mL brown glass bottle. Then 4.0 g of potassium hydroxide (pellet shaped reagent-grade product) was directly added. After the bottle was covered, while being occasionally shaken, the bottle was subjected to an ultrasonic bath for 20 minutes. Thereby the potassium hydroxide was completely dissolved by the alcohol (B), and a 4.0% (wt/vol) potassium hydroxide alcohol solution was prepared. Hereinafter, this solution is called "potassium hydroxide solution (3B)."Furthermore, this preparation operation was performed within 3 hours before measurement of absorbance.

[Measurement of Carbonyl Value]

2.00 g of sample and 23.00 g of reagent-grade n-butanol (A) were fed into a 50 mL screw tube with cap and mixed, to prepare 25.00 g of sample solution (Sa) having a sample concentration of 8 wt. %.

1.250 g of the obtained sample solution (Sa) and 3.750 g of reagent-grade n-butanol (A) were fed into a 50 mL volumetric flask, and mixed, to prepare 5.000 g of sample solution (Sb) having a sample concentration of 2 wt. %.

3 mL of the trichloroacetic acid solution (1A) obtained in Preparation Example 1A and 5 mL of the 2,4-DNPH solution (2A) obtained in Preparation Example 2A were added to the volumetric flask containing 5.000 g of sample solution (Sb) using a volumetric pipette. Furthermore, 1.050 g of purified water was added and mixed to detect precursors of carbonyl compound such as acetal that might be present in the sample as carbonyl by hydrolyzing the precursors.

Next, the volumetric flask was stoppered and a Teflon (registered trademark) seal was wound around the stopper to keep the volumetric flask airtight. Then, the volumetric flask was placed in a 60° C. constant temperature bath and heated for 30 minutes, thereby reacting the 2,4-DNPH and the carbonyls contained in the sample. Next, said volumetric flask was retrieved from the constant temperature bath, and was left standing for 30 minutes at room temperature.

Next, said volumetric flask was opened, and 10 mL of the potassium hydroxide solution (3B) obtained in Preparation Example 3B was added using a volumetric pipette, and then said volumetric flask was shaken to mix the mixture. 8 minutes after the addition of 10 mL of potassium hydroxide solution (3B), reagent-grade n-butanol (A) was added as the diluent solvent. This system was shaken to prepare a total of 50 mL of reaction solution (basic reaction solution). Next, 15 minutes after the addition of 10 mL of potassium hydroxide solution (3B), the reaction solution was placed in an absorption cell (length of liquid layer: 1 cm), and an absorptiometer was used to measure the absorbance at 430 nm ($A_1$).

On the other hand, 5.000 g of reagent-grade n-butanol (A) was used instead of the sample solution (Sb), for blank measurement. A solution obtained by performing the same operations as above (addition of trichloroacetic acid solution (1A), addition of 2,4-DNPH solution (2A), heating and cooling of the obtained mixed solution, addition of potassium hydroxide solution (3B), and addition of a diluent solvent composed of reagent-grade n-butanol (A)) was placed into an absorption cell (length of liquid layer=1 cm), and the absorbance ($A_2$) at 430 nm was measured.

The carbonyl value (COV) was determined by substituting the absorbance ($A_1$) and the absorbance ($A_2$) determined as described above, into the formula CV=($A_1$−$A_2$)/0.1. However, the samples of Practical Example 2, Comparative Example 2, and Comparative Example 3 contain the same amount of caprylyl methicone as modified silicone, so the value resulting from doubling the value calculated based on the formula was set to COV.

Table 1 below lists the total amounts of carbonyl (COV) of the various modified silicone compositions obtained in the practical examples and the comparative examples as well as the results of the evaluation of the aldehyde odors generated after 1 month of storage at room temperature. For the (poly)glycerin-modified silicones of Practical Examples 1 and 2, it was possible to achieve the same degree of deodorization as in Comparative Example 4 where hydrogenation treatment was performed, by only acidizing three times using an aqueous solution of sodium hydrogensulfate monohydrate.

<Glycerin Derivative Group: $R^{*2}$>

$R^{*21}$=—$C_3H_6OCH_2CH(OH)CH_2OH$ $R^{*22}$=—$C_3H_6O$—X, where X is the tetraglycerin derivative portion.

$R^{*23}$=—$C_3H_6O$—X, where X is the triglycerin derivative portion.

<Other Organic Group: $R^{*1}$>

$R^{*11}$=—$C_{12}H_{25}$ $R^{*12}$=—$C_{16}H_{33}$ $R^{*13}$=—$C_2H_4SiMe_2(OSiMe_2)_6OSiMe_3$

Accelerated Odorization Test

It is known that hydrophilic silicone compositions readily generate characteristic odorants over time in formulations that contain water and a specific polyhydric alcohol. Therefore, a simple formulation that incorporated the key materials (Nos. 1 to 3) related to odors was designed as shown in Table 2 below, and samples prepared based thereupon were stored under the accelerated conditions of 1 week at 70° C. The samples were then returned to room temperature and opened, and the strengths and quantities of the generated odors were subjected to functional evaluation by the sense of smell.

TABLE 3

| No. | Name of raw material | Mass (g) |
|---|---|---|
| 1 | Composition containing the modified silicone of Practical Examples 1, 2 or Comparative Examples 1, 2, 3, or 4. | 3.0 |
| 2 | 1,3-butylene glycol | 3.0 |
| 3 | Purified water | 24.0 |
| (4) | (Additive = 7.5% aqueous solution of alkaline buffer) *) | (0 or 0.13) |
|  | Total | 30.0 |

Note
*) Four types of alkaline buffer (trisodium phosphate, tripotassium phosphate, trisodium citrate, and sodium acetate) were used.

TABLE 2

|  | Structure of modified silicone | Odor reduction treatment | Aldehyde odor 1M (RT) | COV (Abs/g) |
|---|---|---|---|---|
| Practical Example 1 | $MD_{72}D^{R*31}{}_9D^{R*21}{}_3M$ (glycerin-modified) | NaHSO4 water treatment | ○ (No) | 0.48 |
| Practical Example 2 | $MD_{330}D^{R*12}{}_{45}D^{R*31}{}_{30}D^{R*22}{}_5M$ (polyglycerin-modified) | NaHSO4 water treatment | ○ (No) | 2.8 |
| Comparative Example 1 | $MD_{72}D^{R*31}{}_9D^{R*21}{}_3M$ (glycerin-modified) | none | xx (Strong) | 14.8 |
| Comparative Example 2 | $MD_{330}D^{R*12}{}_{45}D^{R*31}{}_{30}D^{R*22}{}_5M$ (polyglycerin-modified) | none | x (Yes) | 9.3 |
| Comparative Example 3 | $MD_{330}D^{R*12}{}_{45}D^{R*31}{}_{30}D^{R*22}{}_5M$ (polyglycerin-modified) | Phosphoric acid water treatment | Δ (weak) | 8.1 |
| Comparative Example 4 | $MD_{61}D^{R*11}{}_{12}D^{R*13}{}_2D^{R*23}{}_1M$ (Triglycerin-modified) | Hydrogenation | ○ (No) | 0.92 |

In the table, the structures and types of the functional groups are as follows.

<Group Having a Siloxane Dendron Structure: $R^{*31}$>

$R^{*31}$=—$C_2H_4Si(OSiMe_3)_3$

Preparation of Samples for Accelerated Test

1. Raw material Nos. 1 to 3 of Table 2 were fed into a 50 mL screw tube, which was then stoppered and shaken. Samples were prepared for each modified silicone composition obtained in the Practical Examples and the Comparative Examples.(Total samples: 6)

2. Raw material Nos. 1 to 4 of Table 2 were fed into another 50 mL screw tube, which was then stoppered and shaken. Here, a total of 8 samples were prepared for Practical Examples 1 and 2 by combining each of the 4 types of buffer solutions and the compositions of Practical Examples 1 and 2, and total of 1 sample was prepared for Comparative Example 1 by combining an aqueous solution of trisodium phosphate and the composition of Comparative Example 1.

3. The samples were left standing for 1 week in a constant temperature bath at 70° C.

Odor Test

The samples that were left standing for 1 week in a constant temperature bath at 70° C. as described above were removed and returned to room temperature. The degree of peculiar odors upon opening was evaluated by the sense of smell, in accordance with the following standards.

Odor Test Evaluation Standards:

●: No peculiar odor at all is sensed.

○: A faint peculiar odor is sensed.

Δ: Some peculiar odor is detected.

×: A solvent odor is clearly detected and is unpleasant.

××: A strong solvent odor is detected and is extremely unpleasant.

[Odor Test Results]

The results of the accelerated odorization test in formulations are summarized in the following Table 3, together with the COVs of the modified silicone compositions. In the table, for the section labeled "Odor reduction treatment", the expression "Example [number: X]+[name of alkaline buffer]" indicates the samples for the accelerated test, which contains the sample obtained in Example X and each alkaline buffer.

ization of the formulation was effectively suppressed when the low odor glycerin derivative-modified silicone for which odor reduction treatment of the present invention was performed and an alkaline buffer were used in combination.

[Evaluation of Economic Efficiency]

For each product of Practical Examples 1 and 2 and Comparative Examples 1 to 4, Table 4 below summarizes the number of days of production (also including the cleaning time for reaction vessels, etc.), the number of used reaction vessels, the index values of the costs that reflect the raw material costs and the processing costs (expressed as a ratio, with the total cost of Comparative Example 1 as 1), and the odor reduction effects.

Here, for "Effect," the evaluations of the odor test of Table 3 are entered in Table 4, with ●=5 points, ○=4 points, Δ=3 points, ×=2 points, and ××=1 point.

The economic efficiency (%) was determined as follows: the value $W_1$, which was roughly calculated by the formula "effect/(No. of production days+No. of reaction vessels+cost)," was divided by the value $W_0$, which was obtained by using the same formula for Comparative Example 1 or Comparative Example 2 which lacked odor reduction treatment, based on the molecular weight of the modified silicone, and then multiplied by 100. This revealed the cost vs. effect of each production method.

Specifically, Comparative Example 1, which lacked odor reduction treatment, is for the low molecular weight type, and is calculated to be $W_0=1/(0.5+1+1)=0.40$; and Comparative Example 2, which lacked odor reduction treatment, is for the high molecular weight type, and is calculated to be $W_0=2/(1.5+1+2)=0.44$. Furthermore, for NaHSO4 water treatment—Practical Example 1 (low molecular weight type), the calculation is $W_1=4/(1+1+1.2)=1.3$, so economic efficiency (%)=$100 \times W_1/W_0=100 \times 1.3/0.40=325\%$. Also, for NaHSO4 water treatment—Practical Example 2 (high

TABLE 4

| Sample | Structure of modified silicone | Odor reduction treatment | Odor test (formulation) | COV (Abs/g) |
|---|---|---|---|---|
| Practical Example 1 | $MD_{72}D^{R*31}_{9}D^{R*21}_{3}M$ (glycerin-modified) | NaHSO4 water treatment | ○ | 0.48 |
| | | Practical Example 1 + Na3PO4 | ● | |
| | | Practical Example 1 + K3PO4, trisodium citrate, sodium acetate | ● through ○ | |
| Practical Example 2 | $MD_{330}D^{R*12}_{45}D^{R*31}_{30}D^{R*22}_{5}M$ (polyglycerin-modified) | NaHSO4 water treatment | ○~Δ | 2.8 |
| | | Practical Example 2 + Na3PO4 | ● through ○ | |
| | | Practical Example 2 + K3PO4, trisodium citrate, sodium acetate | ○ | |
| Comparative Example 1 | $MD_{72}D^{R*31}_{9}D^{R*21}_{3}M$ (glycerin-modified) | none | ×× | 14.8 |
| | | Comparative Example 1 + Na3PO4 | Δ through × | |
| Comparative Example 2 | $MD_{330}D^{R*12}_{45}D^{R*31}_{30}D^{R*22}_{5}M$ (polyglycerin-modified) | none | × | 9.3 |
| Comparative Example 3 | $MD_{330}D^{R*12}_{45}D^{R*31}_{30}D^{R*22}_{5}M$ (polyglycerin-modified) | Phosphoric acid water treatment | × | 8.1 |
| Comparative Example 4 | $MD_{61}D^{R*11}_{12}D^{R*13}_{2}D^{R*23}_{1}M$ (Triglycerin-modified) | Hydrogenation | ● | 0.92 |

Based on these results, it was found that the COV and the degree of odorization over time in the formulations correlate extremely well. Furthermore, it was evident that the odor-molecular weight type), the calculation is $W_1=3.5/(2+1+2.2)=0.67$, so economic efficiency (%)=$100 \times W_1/W_0=100 \times 0.67/0.44=152\%$.

TABLE 4

| Odor reduction technology | No. | Structure of modified silicone | No. of production days | No. of reaction vessels | Cost | Effects | Economic efficiency (%) |
|---|---|---|---|---|---|---|---|
| NaHSO4 water treatment | Practical Example 1 | $MD_{72}D^{R*31}{}_9D^{R*21}{}_3M$ (glycerin-modified) | 1 | 1 | 1.2 | 4 | 325 |
| | Practical Example 2 | $MD_{330}D^{R*12}{}_{45}D^{R*31}{}_{30}D^{R*22}{}_5M$ (polyglycerin-modified) | 2 | 1 | 2.2 | 3.5 | 152 |
| NaHSO4 treatment + Na3PO4 | Practical Example 1 | $MD_{72}D^{R*31}{}_9D^{R*21}{}_3M$ (glycerin-modified) | 1 | 1 | 1.2 | 5 | 400 |
| | Practical Example 2 | $MD_{330}D^{R*12}{}_{45}D^{R*31}{}_{30}D^{R*22}{}_5M$ (polyglycerin-modified) | 2 | 1 | 2.2 | 4.5 | 198 |
| none | Comparative Example 1 | $MD_{72}D^{R*31}{}_9D^{R*21}{}_3M$ (glycerin-modified) | 0.5 | 1 | 1 | 1 | 100 |
| | Comparative Example 2 | $MD_{330}D^{R*12}{}_{45}D^{R*31}{}_{30}D^{R*22}{}_5M$ (polyglycerin-modified) | 1.5 | 1 | 2 | 2 | 100 |
| Phosphoric acid water treatment | Comparative Example 3 | $MD_{330}D^{R*12}{}_{45}D^{R*31}{}_{30}D^{R*22}{}_5M$ (polyglycerin-modified) | 2 | 1 | 2.2 | 2 | 86 |
| Hydrogenation | Comparative Example 4 | $MD_{61}D^{R*11}{}_{12}D^{R*13}{}_2D^{R*23}{}_1M$ (Triglycerin-modified) | 3 | 3 | 5 | 5 | 113 |

As is evident from Tables 3 and 4, for the low odor glycerin derivative-modified silicone obtained in Practical Example 1, both the odor and the carbonyl value (COV) were dramatically reduced by the production method of the present invention, and the cost vs. effect was extremely superior. Specifically, when the economic efficiency (%) of Comparative Example 1, which lacked odor reduction treatment, was taken as 100, in the case where deodorizing treatment based on hydrogenation was performed, a very high effect was obtained, but the cost also became very high. As a result, therefore, the economic efficiency (%) remained at 113. That is, from the standpoint of purchasing and using such raw materials, the composition of the Comparative Example 1 was less attractive material. On the other hand, the economic efficiency (%) of Practical Example 1, which performed the NaHSO4 treatment of the present invention, was 325%. Furthermore, when Na3PO4 was used in combination, the economic efficiency (%) reached as high as 400%, so a dramatic improvement in cost vs. effect was observed, compared with untreated products.

In addition, the low odor glycerin derivative-modified silicone obtained in Practical Example 2 had high molecular weight and had gum-like properties even when diluted to 50%. However, it was verified that, even for these silicones for which it is normally difficult to perform odor reduction, more satisfactory odor reduction was achieved by the production method of the present invention. The low odor glycerin derivative-modified silicone obtained in Practical Example 2 was most superior in cost vs. effect among the silicones having high molecular weight. Specifically, when the economic efficiency (%) of Comparative Example 2, which lacked odor reduction treatment, was taken as 100, in the case where odor reduction treatment by phosphoric acid water treatment was performed, cost vs. effect was not satisfactory, and the economic efficiency (%) was 86, which resulted in failure to reach even the original standard value. Although the case of hydrogenation in the high molecular weight type is not shown, it is believed to be impossible to exceed 113, the economic efficiency (%) of the low molecular weight type (Comparative Example 4). In contrast, the economic efficiency (%) of Practical Example 2, which performed the NaHSO4 treatment of the present invention, was 152%, and when Na3PO4 was concomitantly used in this treatment, the economic efficiency (%) reached 198%. Compared with untreated products, a drastic improvement in cost vs. effect was observed.

Furthermore, the low odor glycerin derivative-modified silicone obtained in Practical Examples 1 and 2 has a superior characteristic that, not only in the modified silicone composition itself but also in a water-system composition containing the modified silicone composition, generation of peculiar odors over time or due to high temperature is very little. Therefore, the low odor glycerin derivative-modified silicone obtained in Practical Examples 1 and 2 was verified to be extremely useful as a raw material for external use preparation compositions, including cosmetic compositions.

Hereinafter, formulation examples of the cosmetic composition and the external use preparation according to the present invention are described, but it is understood that the cosmetic composition and the external use preparation according to the present invention are not limited to the types and compositions recited in these formulation examples.

Formulations Already Disclosed in Previous Applications

The low odor glycerin derivative-modified silicone of the present invention can be used for various external use preparations and cosmetic compositions. Specific formulation examples thereof include those obtained by replacing components corresponding to silicone compounds No. 1 to No. 16 in the various external use preparation and cosmetic composition formulations disclosed by the applicants in the practical examples and so on in the above-mentioned Patent Document 21 (WO 2011/049248) with the above-mentioned low odor glycerin derivative-modified silicones according to the present invention (low odor glycerin derivative-modified silicones No. 1 and/or No. 2), and such examples are encompassed by the scope of the invention of the present application as formulation examples of the cosmetic composition or external use preparation according to the present invention. Also, those obtained by replacing components corresponding to silicone compounds No. 1 to No. 16 in the various external use preparation and cosmetic composition in the practical examples and formulation examples in the above-mentioned Patent Document 21 (WO 2011/049248; disclosed by the applicants) with low odor glycerin derivative-modified silicones obtained by treating the silicone compounds No. 1 to No. 13 disclosed in the practical examples and so on in the above-mentioned Patent Document 21 with the production method of the present invention are also encompassed by the scope of the invention of the present application as formulation examples of the cosmetic composition or external use preparation according to the present invention.

Specifically, the practical examples and so on in the above-mentioned Patent Document 21 disclose milky lotions, lip glosses, oil-based foundations, water-in-oil emulsion transparent anti-perspirant compositions, and nonaqueous stick-form anti-perspirant compositions as compositions able to be replaced by the low odor glycerin derivative-modified silicone according to the present invention, and paragraphs [0459] to [0501] in the above-mentioned Patent Document 21 also disclose the following formulation examples. By using compositions comprising the low odor glycerin derivative-modified silicone of the present invention, there is a significant advantage that, in addition to the original effect of the formulation, there is almost no odorization over time in the formulation, and there is almost no change over time in the smell.

Example 1: Emulsion foundation
Example 2: Liquid foundation
Example 3: Foundation
Example 4: Water-in-oil cream
Example 5: Water-in-oil emulsion composition
Example 6: Water-in-oil emulsion rouge (liquid)
Example 7: Liquid rouge
Example 8: Rouge
Example 9: Sunscreen emulsion
Example 10: Emulsion
Example 11: UV blocking cream
Example 12: UV blocking water-in-oil emulsion
Example 13: Sunscreen agent
Example 14: Water-in-oil emulsion sunscreen
Example 15: O/W cream
Example 16: Eye shadow
Example 17: Mascara
Example 18: Mascara
Example 19: Solid powder eye shadow
Example 20: Pressed powder cosmetic
Example 21: Powder foundation
Example 22: Pressed foundation
Example 23: Cream
Example 24: Foundation
Example 25: Water-in-oil emulsion-type sunscreen
Example 26: Lipstick
Example 27: Rouge
Example 28: Foundation
Example 29: Anti-perspirant aerosolized cosmetic composition
Example 30: Nonaqueous pressurized anti-perspirant product
Example 31: Aerosol type anti-perspirant composition
Example 32: Anti-perspirant lotion composition
Example 33: W/O emulsion-type skin external use preparation
Example 34: Nonaqueous anti-perspirant deodorant stick composition
Example 35: W/O solid anti-perspirant stick composition
Example 36: W/O emulsion type anti-perspirant cream composition
Example 37: Mascara
Example 38: Aftershave cream
Example 39: Solid foundation
Example 40: Daytime use skin-lightening cream
Example 41: Sun tanning cream
Example 42: Polyol/O-type nonaqueous emulsion skin external use preparation
Example 43: Polyol/O-type nonaqueous emulsion skin external use preparation Other specific formulation examples thereof include those obtained by replacing components corresponding to silicone compounds No. 1 to No. 14 in the various external use preparation and cosmetic composition formulations disclosed by the applicants in the practical examples and so on in the above-mentioned Patent Document 20 (WO 2011/049247) with the above-mentioned low odor glycerin derivative-modified silicone according to the present invention (low odor glycerin derivative-modified silicone P2), and such examples are encompassed by the scope of the invention of the present application as formulation examples of the cosmetic composition or external use preparation according to the present invention. Also, those obtained by replacing components corresponding to silicone compounds No. 1 to No. 14 in the various external use preparation and cosmetic composition in the practical examples and formulation examples in the above-mentioned Patent Document 20 (WO 2011/049247; disclosed by the applicants) with low odor glycerin derivative-modified silicones obtained by treating the silicone compounds No. 1 to No. 12 and No. 14 disclosed in the practical examples and so on in the above-mentioned Patent Document 20 with the production method of the present invention are also encompassed by the scope of the invention of the present application as formulation examples of the cosmetic composition or external use preparation according to the present invention.

Specifically, as compositions replaceable by the low odor glycerin derivative-modified silicone of the present invention, lipsticks, gel-like compositions, emulsified cosmetic compositions, and water-in-oil emulsion type semitransparent soft gel antiperspirants are disclosed in the practical examples and so on in the above-mentioned Patent Document 20. In addition, the following formulation examples are disclosed in paragraphs [0376] to [0400]. By using compositions comprising the low odor glycerin derivative-modified silicone of the present invention, there is a significant advantage that, in addition to the original effect of the formulation, there is almost no odorization over time in the formulation, and there is almost no change over time in the smell.

Example 1: Rouge
Example 2: Lipstick
Example 3: Rouge
Example 4: Rouge
Example 5: Oil-based solid eye shadow
Example 6: Eye liner
Example 7: Foundation
Example 8: Foundation
Example 9: Gel-like cosmetic composition
Example 10: Cream-like emulsion cosmetic composition
Example 11: Paste-like emulsion cosmetic composition
Example 12: Aerosol type anti-perspirant composition
Example 13: Gel-like anti-perspirant stick
Example 14: Oil-based gel type cleansing agent
Example 15: Gel-like anti-perspirant stick
Example 16: Gel-like deodorant stick
Example 17: Gel-like cream
Example 18: Gel-like lip cream
Example 19: Mascara
Example 20: Gel-like aftershave cream
Example 21: Solid foundation
Example 22: Gel-like daytime use skin-lightening cream
Example 23: Polyol/O-type nonaqueous gel emulsion skin external use preparation Example 24: Polyol/O-type nonaqueous gel emulsion skin external use preparation
Other Formulations
In addition, for example, it is also possible to design formulations having the following hydrocarbon type cosmetic composition base materials as the main constituents, by using low odor glycerin derivative-modified silicone No. 1 (Practical Example 1) of the present invention. Furthermore, if all of the following polyether-modified silicone is replaced by low odor glycerin derivative-modified silicone No. 1, it is also possible to design PEG-free formulations.
[Formulation Example: Liquid Foundation (W/O)]
(Components)

| | | |
|---|---|---|
| 1. Isododecane | 20 parts | |
| 2. Isohexadecane | 10 parts | |
| 3. Isotridecyl isononanoate | 3 parts | |
| 4. Glyceryl tricapryl-caprate | 2 parts | |
| 5. Polyether-modified silicone*[1] | 1.5 parts | |
| 6. Low odor glycerin derivative-modified silicone No. 1 | 0.5 part | |
| 7. Organomodified clay mineral (Bentone 38V) | 1.5 parts | |
| 8. Octyl methoxycinnamate | 5 parts | |
| 9. Octylsilane treated titanium oxide | 8.5 parts | |
| 10. Octylsilane treated red iron oxide | 0.4 parts | |
| 11. Octylsilane treated yellow iron oxide | 1 part | |
| 12. Octylsilane treated black iron oxide | 0.1 parts | |
| 13. Dimethicone, dimethicone crosspolymer*[2] | 2 parts | |
| 14. Copolymer of isododecane and (acrylates/polytrimethylsiloxy methacrylate)*[3] | 1 part | |
| 15. Trimethylsiloxysilicate | 1 part | |
| 16. 1,3-butylene glycol | 5 parts | |
| 17. Glycerin | 3 parts | |
| 18. Sodium chloride | 0.5 part | |
| 19. Preservative | q.s. | |
| 20. Purified water | Remainder | |
| 21. Perfume | q.s. | |

Note
*[1]ES-5300, manufactured by Dow Corning Toray Co., Ltd.
Note
*[2]DC9045, manufactured by Dow Corning
Note
*[3]FA-4002ID, manufactured by Dow Corning Toray Co., Ltd.

Production Method
Step 1: Components 1, 2, 5, 6, 7, 8, 13, 14, and 15 are agitated and mixed.
Step 2: Components 3, 4, and 9 to 12 are kneaded and mixed using a three-roll mill.
Step 3: While agitating, add the compound of Step 2 to the compound obtained in Step 1 and agitate/mix further.
Step 4: Add an aqueous phase formed by uniformly dissolving components 16 to 21 to the mixture obtained in Step 3, emulsify, and fill a container with the emulsion. Thus, a product is obtained.
The obtained W/O type liquid foundation has no unpleasant odor, has excellent emulsion stability when used, has excellent moisture resistance and cosmetic durability, has excellent texture, masks wrinkles, has a light feeling to touch and has excellent adhesion.

The invention claimed is:
1. A method of producing a glycerin derivative-modified silicone or a composition comprising the same, the method comprising treating a glycerin derivative-modified silicone or a composition comprising the same with at least one acidic inorganic salt, wherein the acidic inorganic salt is solid at 25° C. and is water soluble, and a pH at 25° C. of an aqueous solution prepared by dissolving 50 g of the acidic inorganic salt in 1 L of ion exchanged water is 4 or lower, wherein said acidic inorganic salt is at least an acidic inorganic salt comprising hydrogensulfate ions ($HSO_4^-$) and monovalent cations ($M^+$) and wherein the glycerin derivative-modified silicone is a glycerin derivative-modified silicone expressed by the following general formula (1):

wherein $R^1$ represents a monovalent organic group, however, excluding $R^2$, L, and Q, a hydrogen atom or a hydroxyl group; and $R^2$ is a substituted or unsubstituted, straight or branched monovalent hydrocarbon group having 9 to 60 carbon atoms, or the chain organosiloxane group represented by the following general formula (2-1):

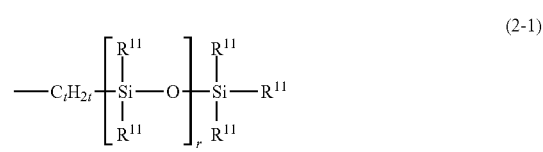

wherein $R^{11}$ are each independently substituted or unsubstituted monovalent hydrocarbon groups having from 1 to 30 carbons, hydroxyl groups, or hydrogen atoms and at least one of the $R^{11}$ moieties is the monovalent hydrocarbon group; t is a number in a range of 2 to 10; and r is a number in a range of 1 to 500; or the general formula (2-2) below:

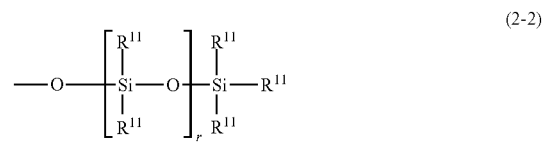

wherein, $R^{11}$ and r are as defined above; and $L^1$ represents a silylalkyl group having a siloxane dendron structure expressed by the following general formula (3) when i=1;

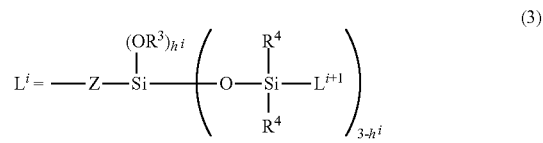

wherein, $R^3$ each independently represents a substituted or unsubstituted, straight or branched monovalent hydrocarbon group having 1 to 30 carbons; $R^4$ each independently represents an alkyl group or phenyl group having 1 to 6 carbon atoms; Z represents a divalent organic group; i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^4$ when i=k, and $h^i$ is a number in a range from 0 to 3); Q represents a glycerin derivative group-containing organic group; and
a, b, c, and d are numbers within the respective ranges $1.0 \leq a \leq 2.5$, $0 \leq b \leq 1.5$, $0.0001 \leq c \leq 1.5$, and $0.0001 \leq d \leq 1.5$.

2. A method of producing a glycerin derivative-modified silicone or a composition comprising the same, wherein the method of producing a glycerin derivative-modified silicone or a composition comprising the same according to claim 1 further comprises a process [A] that synthesizes the glycerin derivative-modified silicone or a composition comprising the same by subjecting to a hydrosilylation reaction:
  (a) a glycerin derivative having a carbon-carbon double bond at a terminal of the molecular chain and
  (b) an organohydrogenpolysiloxane; and
  a process [B] that, together with said synthesis process [A] or after said synthesis process [A], treats the glycerin derivative-modified silicone or a composition comprising the same in the presence of at least one (c) acidic inorganic salt, wherein the acidic inorganic salt is solid at 25° C. and is water soluble, and a pH at 25° C. of an aqueous solution prepared by dissolving 50 g of the acidic inorganic salt in 1 L of ion exchanged water is 4 or lower, wherein said acidic inorganic salt is at least an acidic inorganic salt comprising hydrogensulfate ions ($HSO_4^-$) and monovalent cations ($M^+$).

3. The method of producing a glycerin derivative-modified silicone or a composition comprising the same according to claim 1, comprising removing odor-causing substances by heating or depressurizing after the treatment process that uses said acidic inorganic salt.

4. The method of producing a glycerin derivative-modified silicone or a composition comprising the same according to claim 1, wherein said acidic inorganic salt is at least an acidic inorganic salt selected from the group consisting of sodium hydrogensulfate, potassium hydrogensulfate, and ammonium hydrogensulfate.

5. The method of producing a glycerin derivative-modified silicone or a composition comprising the same according to claim 1, wherein the used amount of said acidic inorganic salt is in a range from 100 ppm to 10,000 ppm for the glycerin derivative-modified silicone or a composition comprising the same.

6. The method of producing a glycerin derivative-modified silicone or a composition comprising the same according to claim 1, comprising performing the treatment process that uses said acidic inorganic salt in the presence of water and/or a hydrophilic medium.

7. A method of producing a glycerin derivative-modified silicone or a composition comprising the same, further comprising adding an alkaline buffer, in an amount corresponding to 100 ppm to 50,000 ppm, to the glycerin derivative-modified silicone or a composition comprising the same obtained by the method according to claim 1.

8. The method of producing a glycerin derivative-modified silicone or a composition comprising the same according to claim 1, wherein, in said general formula (1), the silylalkyl group having the siloxane dendron structure indicated by $L^1$ is a functional group expressed by the general formula (3-1) below:

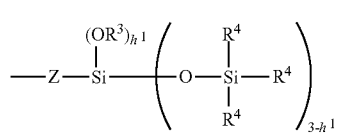
(3-1)

or general formula (3-2) below:

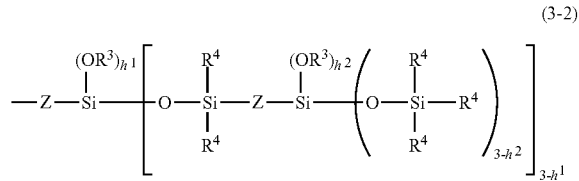
(3-2)

wherein, $R^3$, $R^4$, and Z are as defined above, and $h^1$ and $h^2$ are each independently a number in a range from 0 to 3.

9. The method of producing a glycerin derivative-modified silicone or a composition comprising the same according to claim 1, wherein, in said general formula (1), Q is a glycerin derivative group-containing organic group that is bonded to a silicon atom via a linking group that is at least divalent, and that comprises at least one type of hydrophilic unit that is selected from among the hydrophilic units represented by the following structural formulae (3-3) through (3-5):

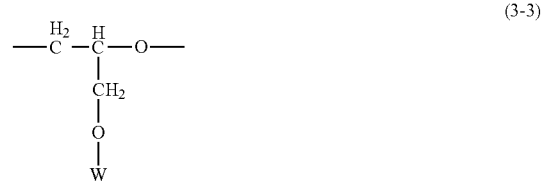
(3-3)

wherein, W is a hydrogen atom or an alkyl group having from 1 to 20 carbon atoms

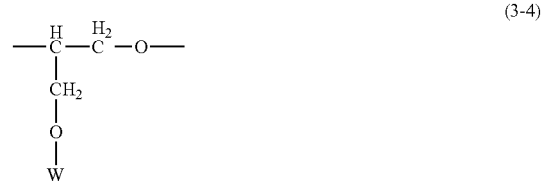
(3-4)

wherein, W is as defined above

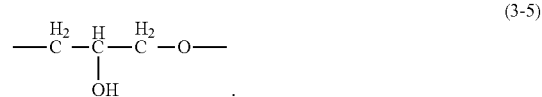
(3-5)

10. The method of producing a glycerin derivative-modified silicone or a composition comprising the same according to claim 9, wherein, in said general formula (1), Q is a hydrophilic segment that is bonded to a silicon atom via a linking group that is at least divalent, and the hydrophilic segment comprising at least one linearly bonded hydrophilic unit is selected from among the hydrophilic units represented by said structural formulae (3-3) through (3-5); or Q is a glycerin derivative group-containing organic group that is bonded to a silicon atom via a linking group that is at least divalent, that contains at least two of one or more type of hydrophilic unit selected from the hydrophilic units represented by said structural formulae (3-3) through (3-5), and a branch unit selected from groups represented by structural formulae (3-6) through (3-8):

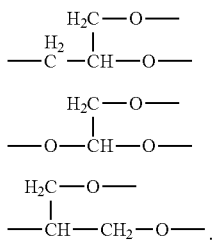

(3-6)

(3-7)

(3-8)

11. An external use preparation raw material or cosmetic composition raw material comprising the glycerin derivative-modified silicone or a composition comprising the same obtained by the production method according to claim 1.

12. An external use preparation or cosmetic composition comprising the glycerin derivative-modified silicone or a composition comprising the same obtained by the method according to claim 1.

13. The external use preparation raw material or cosmetic composition raw material according to claim 11, comprising an alkaline buffer in an amount corresponding to 100 ppm to 50,000 ppm, for the glycerin derivative-modified silicone or a composition comprising the same.

14. A method of measuring a carbonyl value of the glycerin derivative-modified silicone or a composition comprising the same obtained by the method according to claim 1, based on the absorbance of a reaction solution that is obtained by reacting, in a reaction medium, at least one monovalent lower alcohol having 1 to 4 carbon atoms, 2,4-dinitrophenylhydrazine and the carbonyls in the glycerin derivative-modified silicone or a composition comprising the same.

15. A glycerin derivative-modified silicone or a composition comprising the same, which is the glycerin derivative-modified silicone or a composition comprising the same obtained by the method according to claim 1, wherein the carbonyl value measured by the method of measuring the carbonyl value according to claim 14 is less than or equal to 3.0 Abs/g.

16. The external use preparation or cosmetic composition according to claim 12, comprising an alkaline buffer, in an amount corresponding to 100 ppm to 50,000 ppm, for the glycerin derivative-modified silicone or a composition comprising the same.

* * * * *